(12) United States Patent
Curley

(10) Patent No.: US 10,548,654 B2
(45) Date of Patent: Feb. 4, 2020

(54) DEVICES AND METHODS FOR REMOTE TEMPERATURE MONITORING IN FLUID ENHANCED ABLATION THERAPY

(71) Applicant: Thermedical, Inc., Waltham, MA (US)

(72) Inventor: Michael G. Curley, Weston, MA (US)

(73) Assignee: Thermedical, Inc., Waltham, MA (US)

( * ) Notice: Subject to any disclaimer, the term of this patent is extended or adjusted under 35 U.S.C. 154(b) by 372 days.

(21) Appl. No.: 15/450,806

(22) Filed: Mar. 6, 2017

(65) Prior Publication Data

US 2017/0238993 A1 Aug. 24, 2017

Related U.S. Application Data

(63) Continuation of application No. 13/445,034, filed on Apr. 12, 2012, now abandoned.
(Continued)

(51) Int. Cl.
*A61B 18/14* (2006.01)
*A61B 18/04* (2006.01)
(Continued)

(52) U.S. Cl.
CPC ............ *A61B 18/04* (2013.01); *A61B 18/082* (2013.01); *A61B 18/1477* (2013.01);
(Continued)

(58) Field of Classification Search
CPC ......... A61B 18/04; A61B 18/12; A61B 18/14; A61B 18/1477; A61B 2018/044;
(Continued)

(56) References Cited

U.S. PATENT DOCUMENTS

| 4,160,455 A | 7/1979 | Law |
| 4,424,190 A | 1/1984 | Mather, III et al. |

(Continued)

FOREIGN PATENT DOCUMENTS

| CN | 1323233 A | 11/2001 |
| CN | 1341462 A | 3/2002 |

(Continued)

OTHER PUBLICATIONS

European Office Action for Application No. EP 12771876.5, dated May 31, 2018 (6 pages).
(Continued)

*Primary Examiner* — Eugene T Wu
(74) *Attorney, Agent, or Firm* — Nutter McClennan & Fish LLP

(57) ABSTRACT

Devices and methods for monitoring the temperature of tissue at various locations in a treatment volume during fluid enhanced ablation therapy are provided. In one embodiment, an ablation device is provided having an elongate body, at least one ablation element, and at least one temperature sensor. The elongate body includes a proximal and distal end, an inner lumen, and at least one outlet port to allow fluid to be delivered to tissue surrounding the elongate body. The at least one ablation element is configured to heat tissue surrounding the at least one ablation element. The at least one temperature sensor can be positioned a distance away from the at least one ablation element and can be effective to output a measured temperature of tissue spaced a distance apart from the at least one ablation element such that the measured temperature indicates whether tissue is being heating to a therapeutic level.

19 Claims, 13 Drawing Sheets

Related U.S. Application Data

(60) Provisional application No. 61/474,574, filed on Apr. 12, 2011.

(51) Int. Cl.

| | | |
|---|---|---|
| *A61B 18/08* | (2006.01) | |
| *A61B 18/16* | (2006.01) | |
| *F04B 17/03* | (2006.01) | |
| *A61B 18/00* | (2006.01) | |
| *A61B 17/00* | (2006.01) | |
| *F04B 19/22* | (2006.01) | |
| *F04B 43/04* | (2006.01) | |
| *F04B 49/06* | (2006.01) | |

(52) U.S. Cl.
CPC .............. *A61B 18/16* (2013.01); *F04B 17/03* (2013.01); *A61B 2017/00526* (2013.01); *A61B 2018/00029* (2013.01); *A61B 2018/00041* (2013.01); *A61B 2018/00577* (2013.01); *A61B 2018/00642* (2013.01); *A61B 2018/00773* (2013.01); *A61B 2018/00791* (2013.01); *A61B 2018/00797* (2013.01); *A61B 2018/00809* (2013.01); *A61B 2018/00821* (2013.01); *A61B 2018/046* (2013.01); *A61B 2018/1425* (2013.01); *A61B 2018/162* (2013.01); *F04B 19/22* (2013.01); *F04B 43/04* (2013.01); *F04B 49/06* (2013.01); *F04C 2270/041* (2013.01); *Y10T 29/49016* (2015.01); *Y10T 29/49085* (2015.01)

(58) Field of Classification Search
CPC ...... A61B 2018/046; A61B 2018/1472; A61B 2018/00577; A61B 2018/00714; A61B 2018/00797; A61B 2018/00803; A61B 2018/00809; A61B 2018/00815; A61B 2018/00821; A61B 2018/1425; A61B 2018/1427; A61B 2018/143; A61B 2018/1432; A61B 2018/00791
See application file for complete search history.

(56) References Cited

U.S. PATENT DOCUMENTS

| | | | |
|---|---|---|---|
| 5,190,538 | A | 3/1993 | Hussein et al. |
| 5,271,413 | A | 12/1993 | Dalamagas et al. |
| 5,336,222 | A | 8/1994 | Durgin, Jr. et al. |
| 5,403,311 | A | 4/1995 | Abele et al. |
| 5,409,487 | A | 4/1995 | Jalbert et al. |
| 5,431,648 | A | 7/1995 | Lev |
| 5,431,649 | A | 7/1995 | Mulier et al. |
| 5,437,629 | A | 8/1995 | Goldrath |
| 5,437,673 | A | 8/1995 | Baust et al. |
| 5,449,380 | A | 9/1995 | Chin |
| 5,456,682 | A | 10/1995 | Edwards et al. |
| 5,458,597 | A | 10/1995 | Edwards et al. |
| 5,462,521 | A | 10/1995 | Brucker et al. |
| 5,472,441 | A | 12/1995 | Edwards et al. |
| 5,496,271 | A | 3/1996 | Burton et al. |
| 5,522,815 | A | 6/1996 | Durgin, Jr. et al. |
| 5,545,195 | A | 8/1996 | Lennox et al. |
| 5,549,559 | A | 8/1996 | Eshel |
| 5,609,151 | A | 3/1997 | Mulier et al. |
| 5,653,692 | A | 8/1997 | Masterson et al. |
| 5,728,143 | A | 3/1998 | Gough et al. |
| 5,735,846 | A | 4/1998 | Panescu et al. |
| 5,800,482 | A | 9/1998 | Pomeranz et al. |
| 5,827,269 | A | 10/1998 | Saadat |
| 5,891,094 | A * | 4/1999 | Masterson ............. A61B 18/08 604/113 |
| 5,891,134 | A | 4/1999 | Goble et al. |
| 5,944,713 | A | 8/1999 | Schuman |
| 5,954,719 | A | 9/1999 | Chen et al. |
| 5,964,791 | A | 10/1999 | Bolmsjo |
| 6,024,743 | A | 2/2000 | Edwards |
| 6,030,379 | A | 2/2000 | Panescu et al. |
| 6,032,077 | A | 2/2000 | Pomeranz |
| 6,033,383 | A | 3/2000 | Ginsburg |
| 6,045,549 | A | 4/2000 | Smethers et al. |
| 6,056,746 | A | 5/2000 | Goble et al. |
| 6,071,280 | A | 6/2000 | Edwards et al. |
| 6,080,151 | A | 6/2000 | Swartz et al. |
| 6,090,106 | A | 7/2000 | Goble et al. |
| 6,112,123 | A | 8/2000 | Kelleher et al. |
| 6,119,041 | A | 9/2000 | Pomeranz et al. |
| 6,139,570 | A | 10/2000 | Saadat et al. |
| 6,139,571 | A | 10/2000 | Fuller et al. |
| 6,179,803 | B1 | 1/2001 | Edwards et al. |
| 6,208,881 | B1 | 3/2001 | Champeau |
| 6,233,490 | B1 | 5/2001 | Kasevich |
| 6,238,393 | B1 | 5/2001 | Mulier et al. |
| 6,272,370 | B1 | 8/2001 | Gillies et al. |
| 6,302,904 | B1 | 10/2001 | Wallsten et al. |
| 6,315,777 | B1 | 11/2001 | Comben |
| 6,328,735 | B1 | 12/2001 | Curley et al. |
| 6,337,994 | B1 | 1/2002 | Stoianovici et al. |
| 6,358,273 | B1 | 3/2002 | Strul et al. |
| 6,405,067 | B1 | 6/2002 | Mest et al. |
| 6,409,722 | B1 | 6/2002 | Hoey et al. |
| 6,411,852 | B1 | 6/2002 | Danek et al. |
| 6,443,947 | B1 | 9/2002 | Marko et al. |
| 6,463,332 | B1 | 10/2002 | Aldrich |
| 6,464,694 | B1 | 10/2002 | Massengill |
| 6,468,274 | B1 | 10/2002 | Alleyne et al. |
| 6,475,213 | B1 | 11/2002 | Whayne et al. |
| 6,477,396 | B1 | 11/2002 | Mest et al. |
| 6,494,902 | B2 | 12/2002 | Hoey et al. |
| 6,514,251 | B1 | 2/2003 | Ni et al. |
| 6,529,756 | B1 | 3/2003 | Phan et al. |
| 6,564,096 | B2 | 5/2003 | Mest |
| 6,565,561 | B1 | 5/2003 | Goble et al. |
| 6,603,997 | B2 | 8/2003 | Doody |
| 6,620,155 | B2 | 9/2003 | Underwood et al. |
| 6,641,580 | B1 | 11/2003 | Edwards et al. |
| 6,669,685 | B1 | 12/2003 | Rizoiu et al. |
| 6,678,552 | B2 | 1/2004 | Pearlman |
| 6,702,810 | B2 | 3/2004 | McClurken et al. |
| 6,752,802 | B1 | 6/2004 | Isenberg et al. |
| 6,772,012 | B2 | 8/2004 | Ricart et al. |
| 6,814,730 | B2 | 11/2004 | Li |
| 6,904,303 | B2 | 6/2005 | Phan et al. |
| 6,972,014 | B2 | 12/2005 | Eum et al. |
| 7,001,378 | B2 | 2/2006 | Yon et al. |
| 7,070,597 | B2 | 7/2006 | Truckai et al. |
| 7,101,369 | B2 | 9/2006 | van der Welde |
| 7,160,259 | B2 | 1/2007 | Tardy et al. |
| 7,179,256 | B2 | 2/2007 | Mest |
| 7,207,989 | B2 | 4/2007 | Pike, Jr. et al. |
| 7,244,254 | B2 | 7/2007 | Brace et al. |
| 7,270,659 | B2 | 9/2007 | Ricart et al. |
| 7,311,703 | B2 | 12/2007 | Turovskiy et al. |
| 7,387,625 | B2 | 6/2008 | Hovda et al. |
| 7,387,630 | B2 | 6/2008 | Mest |
| 7,412,273 | B2 | 8/2008 | Jais et al. |
| 7,416,552 | B2 | 8/2008 | Paul et al. |
| 7,559,905 | B2 | 7/2009 | Kagosaki et al. |
| 7,604,634 | B2 | 10/2009 | Hooven |
| 7,879,030 | B2 | 2/2011 | Paul et al. |
| 7,938,822 | B1 | 5/2011 | Berzak et al. |
| 7,951,143 | B2 | 5/2011 | Wang et al. |
| 7,993,335 | B2 | 8/2011 | Rioux et al. |
| 8,128,620 | B2 | 3/2012 | Wang et al. |
| 8,128,621 | B2 | 3/2012 | Wang et al. |
| 8,273,082 | B2 | 9/2012 | Wang et al. |
| 8,287,531 | B2 | 10/2012 | Mest |
| 8,333,762 | B2 | 12/2012 | Mest et al. |
| 8,369,922 | B2 | 2/2013 | Paul et al. |
| 8,439,907 | B2 | 5/2013 | Auth et al. |
| 8,444,638 | B2 | 5/2013 | Woloszko et al. |
| 8,449,535 | B2 | 5/2013 | Deno et al. |
| 8,515,560 | B2 | 8/2013 | Debruyne et al. |

(56) References Cited

U.S. PATENT DOCUMENTS

| | | |
|---|---|---|
| 8,591,507 B2 | 11/2013 | Kramer et al. |
| 8,663,226 B2 | 3/2014 | Germain |
| 8,700,133 B2 | 4/2014 | Hann |
| 8,702,697 B2 | 4/2014 | Curley |
| 8,755,860 B2 | 6/2014 | Paul et al. |
| 8,758,349 B2 | 6/2014 | Germain et al. |
| 8,864,760 B2 | 10/2014 | Kramer et al. |
| 8,945,121 B2 | 2/2015 | Curley |
| 9,033,972 B2 | 5/2015 | Curley |
| 9,125,671 B2 | 9/2015 | Germain et al. |
| 9,138,287 B2 | 9/2015 | Curley et al. |
| 9,138,288 B2 | 9/2015 | Curley |
| 9,445,861 B2 | 9/2016 | Curley |
| 9,610,396 B2 | 4/2017 | Curley et al. |
| 9,730,748 B2 | 8/2017 | Curley |
| 9,743,984 B1 | 8/2017 | Curley et al. |
| 9,877,768 B2 | 1/2018 | Curley et al. |
| 9,937,000 B2 | 4/2018 | Curley |
| 10,022,176 B2 | 7/2018 | Curley |
| 10,058,385 B2 | 8/2018 | Curley |
| 10,307,201 B2 | 6/2019 | Curley |
| 2001/0031946 A1 | 10/2001 | Walker et al. |
| 2002/0120259 A1 | 8/2002 | Lettice et al. |
| 2002/0123749 A1 | 9/2002 | Jain |
| 2002/0153046 A1 | 10/2002 | Dantsker et al. |
| 2002/0183735 A1 | 12/2002 | Edwards et al. |
| 2003/0109871 A1 | 6/2003 | Johnson et al. |
| 2003/0120271 A1 | 6/2003 | Burnside et al. |
| 2004/0006336 A1 | 1/2004 | Swanson |
| 2004/0116922 A1 | 6/2004 | Hovda et al. |
| 2004/0220559 A1 | 11/2004 | Kramer et al. |
| 2004/0230190 A1 | 11/2004 | Dahla et al. |
| 2004/0260282 A1 | 12/2004 | Gough et al. |
| 2005/0015081 A1 | 1/2005 | Turovskiy et al. |
| 2005/0055019 A1 | 3/2005 | Skarda |
| 2005/0059963 A1 | 3/2005 | Phan et al. |
| 2005/0080410 A1 | 4/2005 | Rioux et al. |
| 2005/0165391 A1 | 7/2005 | Maguire et al. |
| 2005/0187599 A1 | 8/2005 | Sharkey et al. |
| 2005/0192652 A1 | 9/2005 | Cioanta et al. |
| 2005/0245923 A1 | 11/2005 | Christopherson et al. |
| 2005/0267552 A1 | 12/2005 | Conquergood et al. |
| 2006/0085054 A1* | 4/2006 | Zikorus ............... A61B 18/08 607/96 |
| 2006/0118127 A1 | 6/2006 | Chinn |
| 2006/0129091 A1 | 6/2006 | Bonnette et al. |
| 2006/0216275 A1 | 9/2006 | Mon |
| 2006/0259024 A1 | 11/2006 | Turovskiy et al. |
| 2006/0276780 A1 | 12/2006 | Brace et al. |
| 2006/0287650 A1 | 12/2006 | Cao et al. |
| 2007/0027448 A1 | 2/2007 | Paul et al. |
| 2007/0032786 A1 | 2/2007 | Francischelli |
| 2007/0167775 A1 | 7/2007 | Kochavi et al. |
| 2007/0185483 A1 | 8/2007 | Butty et al. |
| 2007/0219434 A1 | 9/2007 | Abreu |
| 2007/0250056 A1 | 10/2007 | Vanney |
| 2007/0287998 A1 | 12/2007 | Sharareh et al. |
| 2007/0288075 A1 | 12/2007 | Dowlatshahi |
| 2008/0086073 A1 | 4/2008 | McDaniel |
| 2008/0154258 A1 | 6/2008 | Chang et al. |
| 2008/0161788 A1 | 7/2008 | Dando et al. |
| 2008/0161797 A1 | 7/2008 | Wang et al. |
| 2008/0167650 A1 | 7/2008 | Joshi et al. |
| 2008/0249463 A1 | 10/2008 | Pappone et al. |
| 2008/0275438 A1 | 11/2008 | Gadsby et al. |
| 2008/0275440 A1 | 11/2008 | Kratoska et al. |
| 2008/0288038 A1 | 11/2008 | Paul et al. |
| 2009/0069808 A1 | 3/2009 | Pike, Jr. et al. |
| 2009/0082837 A1 | 3/2009 | Gellman et al. |
| 2009/0093811 A1 | 4/2009 | Koblish et al. |
| 2009/0118725 A1 | 5/2009 | Auth et al. |
| 2009/0118727 A1 | 5/2009 | Pearson et al. |
| 2009/0163836 A1 | 6/2009 | Sliwa |
| 2009/0192507 A1 | 7/2009 | Luttich |
| 2009/0254083 A1 | 10/2009 | Wallace et al. |
| 2010/0030098 A1* | 2/2010 | Fojtik ............... A61B 5/015 600/549 |
| 2010/0094272 A1 | 4/2010 | Rossetto et al. |
| 2010/0198056 A1 | 8/2010 | Fabro et al. |
| 2010/0292766 A1 | 11/2010 | Duong et al. |
| 2010/0324471 A1 | 12/2010 | Flaherty et al. |
| 2011/0060349 A1 | 3/2011 | Cheng et al. |
| 2011/0137150 A1 | 6/2011 | Connor et al. |
| 2011/0160726 A1 | 6/2011 | Ingle |
| 2011/0184403 A1 | 7/2011 | Brannan |
| 2011/0190756 A1 | 8/2011 | Venkatachalam et al. |
| 2011/0230799 A1 | 9/2011 | Christian et al. |
| 2011/0251615 A1 | 10/2011 | Truckai et al. |
| 2011/0270246 A1 | 11/2011 | Clark et al. |
| 2011/0282342 A1 | 11/2011 | Leo et al. |
| 2012/0108938 A1 | 5/2012 | Kauphusman et al. |
| 2012/0130381 A1 | 5/2012 | Germain |
| 2012/0165812 A1 | 6/2012 | Christian |
| 2012/0253188 A1 | 10/2012 | Holland |
| 2012/0265190 A1 | 10/2012 | Curley et al. |
| 2012/0265199 A1 | 10/2012 | Curley |
| 2012/0265200 A1 | 10/2012 | Curley |
| 2012/0265276 A1 | 10/2012 | Curley |
| 2012/0277737 A1 | 11/2012 | Curley |
| 2012/0310230 A1 | 12/2012 | Willis |
| 2014/0052117 A1 | 2/2014 | Curley |
| 2014/0058386 A1 | 2/2014 | Clark et al. |
| 2014/0188106 A1 | 7/2014 | Curley |
| 2014/0275977 A1 | 9/2014 | Curley et al. |
| 2014/0276743 A1 | 9/2014 | Curley |
| 2014/0276758 A1 | 9/2014 | Lawrence et al. |
| 2014/0350542 A1 | 11/2014 | Kramer et al. |
| 2015/0066025 A1 | 3/2015 | Curley |
| 2015/0223882 A1 | 8/2015 | Curley |
| 2015/0351823 A1 | 12/2015 | Curley |
| 2015/0359582 A1 | 12/2015 | Curley et al. |
| 2016/0354138 A1 | 12/2016 | Curley |
| 2017/0296739 A1 | 10/2017 | Curley et al. |
| 2017/0333107 A1 | 11/2017 | Curley |
| 2018/0042669 A1 | 2/2018 | Curley et al. |
| 2018/0140345 A1 | 5/2018 | Curley et al. |
| 2018/0185083 A1 | 7/2018 | Curley |

FOREIGN PATENT DOCUMENTS

| | | |
|---|---|---|
| CN | 1119127 C | 8/2003 |
| CN | 1525839 A | 9/2004 |
| CN | 1897885 A | 1/2007 |
| CN | 101209217 A | 7/2008 |
| CN | 101578073 A | 11/2009 |
| CN | 101773699 A | 7/2010 |
| CN | 201642316 U | 11/2010 |
| CN | 101999931 A | 4/2011 |
| EP | 0 895 756 A1 | 2/1999 |
| EP | 1 033 107 A1 | 9/2000 |
| EP | 0 908 156 B1 | 11/2003 |
| EP | 2 042 112 A2 | 4/2009 |
| EP | 2 430 996 A2 | 3/2012 |
| JP | 62-211057 A | 9/1987 |
| JP | 01-146539 A | 6/1989 |
| JP | 05-212048 A | 8/1993 |
| JP | 10-505268 A | 5/1998 |
| JP | 11-178787 A | 7/1999 |
| JP | 2003-528684 A | 9/2003 |
| JP | 2008-534081 A | 8/2008 |
| JP | 6297971 B2 | 3/2018 |
| WO | 96/07360 A1 | 3/1996 |
| WO | 96/34569 A1 | 11/1996 |
| WO | 96/36288 A1 | 11/1996 |
| WO | 97/29702 A1 | 8/1997 |
| WO | 98/29068 A1 | 7/1998 |
| WO | 99/20191 A1 | 4/1999 |
| WO | 99/32149 A1 | 7/1999 |
| WO | 02/089686 A1 | 11/2002 |
| WO | 03/028524 A3 | 10/2003 |
| WO | 03/096871 A2 | 11/2003 |
| WO | 2005/048858 A1 | 6/2005 |
| WO | 2005/089663 A1 | 9/2005 |
| WO | 2006/031541 A1 | 3/2006 |

(56) References Cited

FOREIGN PATENT DOCUMENTS

| WO | 2006/055658 | A1 | 5/2006 |
|---|---|---|---|
| WO | 2006/095171 | A1 | 9/2006 |
| WO | 2006/102471 | A2 | 9/2006 |
| WO | 2006/103951 | A1 | 10/2006 |
| WO | 2007/080578 | A2 | 7/2007 |
| WO | 2010/002733 | A1 | 1/2010 |
| WO | 2010/151619 | A2 | 12/2010 |
| WO | 2012/071058 | A1 | 5/2012 |

OTHER PUBLICATIONS

Brace CL. Microwave tissue ablation: biophysics, technology, and applications.; Crit Rev Biomed Eng. 2010;38(1):65-78.
Chinese Office Action for Application No. 201280028609.9, dated May 27, 2015. (22 pages).
Chinese Office Action for Application No. 201280028611.6, dated Jul. 29, 2015. (23 pages).
Chinese Office Action for Application No. 201280028612.0, dated Nov. 2, 2016. (8 pages).
Chinese Office Action for Application No. 201280028620.5, dated May 27, 2015. (26 pages).
Chinese Office Action for Application No. 201280028621.X, dated Jul. 31, 2015. (18 pages).
Chinese Office Action for Application No. 201380053690.0, dated Sep. 30, 2016. (17 pages).
Chinese Office Action for Application No. 201380053690.0, dated Jul. 20, 2017. (18 pages).
Extended Search Report and Written Opinion for EP 12770537.4 dated Oct. 10, 2014 (6 pages).
Extended Search Report and Written Opinion for EP 12770631.5 dated Oct. 1, 2014 (6 Pages).
Extended Search Report and Written Opinion for EP 12771331.1 dated Sep. 25, 2014 (6 Pages).
Extended European Search Report and Written Opinion for Application No. 12771601.7 dated Oct. 27, 2014 (7 pages).
Extended Search Report and Written Opinion for EP 12 77 1876 dated Oct. 13, 2014 (6 pages).
Extended European Search Report and Search Opinion for Application No. 13829821.1 dated Mar. 17, 2016 (7 pages).
International Search Report and Written Opinion for Application No. PCT/US2012/033203, dated Sep. 21, 2012. (23 pages).
International Search Report and Written Opinion for Application No. PCT/US2012/033213, dated Sep. 21, 2012. (17 pages).
International Search Report and Written Opinion for Application No. PCT/US2012/033216, dated Sep. 21, 2012. (17 pages).
International Search Report and Written Opinion for Application No. PCT/US2012/033327, dated Sep. 21, 2012. (14 pages).
International Search Report and Written Opinion for Application No. PCT/US2012/033332, dated Sep. 21, 2012. (20 pages).
International Search Report and Written Opinion for Application No. PCT/US2013/053977, dated Nov. 14, 2013. (20 pages).
International Search Report and Written Opinion for Application No. PCT/US2014/024731, dated Jul. 21, 2014 (39 pages).
Japanese Office Action for Application No. 2014-505263, dated Jan. 26, 2016 (4 pages).
Japanese Office Action for Application No. 2014-505266, dated Feb. 23, 2016 (7 pages).
David R. Lide (ed)., CRC Handbook of Chemistry and Physics, 87th Edition. 2006. p. 8-81. CRC Press, Florida.
Nath et al., Prog. Card. Dis. 37(4):185-205 (1995).
Rolf Sander, Compilation of Henry's Law Constants for Inorganic and Organic Species of Potential Importance in Environmental Chemistry. Max-Planck Institute of Chemistry. 1999, Mainz Germany. Www.henrys-law.org.
Sapareto et al., Int. J Rad. One. Biol. Phys. 10(6):787-800 (1984).
Young, S.T., et al., An instrument using variation of resistance to aid in needle tip insertion in epidural block in monkeys. Med Instrum. Oct. 1987;21(5):266-8. Abstract Only.
International Invitation to Pay Additional Fees for Application No. PCT/US2017/044706, dated Oct. 5, 2017 (2 Pages).
Japanese Office Action for Application No. 2017-151156, dated Aug. 7, 2018 (11 pages).
International Search Report and Written Opinion for Application No. PCT/US2017/044706, dated Nov. 29, 2017 (25 pages).
European Office Action for Application No. 12771601.7, dated Jun. 13, 2018 (5 pages).
Japanese Office Action for Application No. 2017-207454, dated Oct. 2, 2018 (6 pages).
Japanese Office Action for Application No. 2018-029767, dated Sep. 4, 2018 (5 pages).
Chinese Office Action for Application No. 2016112115279.0, dated Nov. 30, 2018. (15 pages).
Chinese Office Action for Application No. 201710537279.0, dated Apr. 3, 2019. (8 pages).
Extended European Search Report and Search Opinion for Application No. 19151775.4 dated May 21, 2019 (8 pages).
Japanese Office Action for Application No. 2017-151156, dated Apr. 5, 2019 (23 pages).
U.S. Appl. No. 16/373,104, filed Apr. 2, 2019, Methods and Devices for Use of Degassed Fluids With Fluid Enhanced Ablation Devices.

* cited by examiner

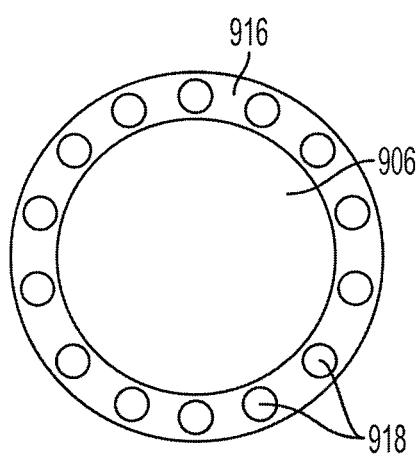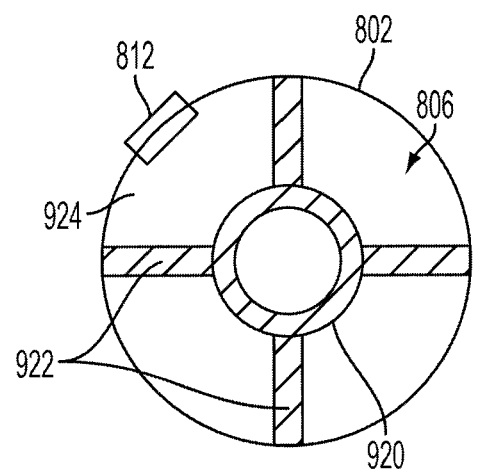
FIG. 9A                    FIG. 9B

DEVICES AND METHODS FOR REMOTE TEMPERATURE MONITORING IN FLUID ENHANCED ABLATION THERAPY

RELATED APPLICATIONS

This application is a continuation of U.S. application Ser. No. 13/445,034, filed on Apr. 12, 2012, and entitled "Devices and Methods for Remote Temperature Monitoring in Fluid Enhanced Ablation Therapy," which claims priority to U.S. Provisional Application No. 61/474,574, filed on Apr. 12, 2011, and entitled "Ablation Catheters." This application is also related to U.S. application Ser. No. 13/445,040, issued as U.S. Pat. No. 8,945,121, entitled "Methods and Devices for Use of Degassed Fluids with Fluid Enhanced Ablation Devices," U.S. application Ser. No. 13/445,036, issued as U.S. Pat. No. 9,138,287, entitled "Methods and Devices for Heating Fluid in Fluid Enhanced Ablation Therapy," U.S. application Ser. No. 13/445,373, issued as U.S. Pat. No. 9,445,861, entitled "Methods and Devices for Controlling Ablation Therapy," and U.S. application Ser. No. 13/445,365, issued as U.S. Pat. No. 8,702,697, entitled "Devices and Methods for Shaping Therapy in Fluid Enhanced Ablation," respectively, and filed concurrently with U.S. application Ser. No. 13/445,034. The disclosures of each of these applications are hereby incorporated by reference in their entirety.

FIELD

The present invention relates generally to fluid enhanced ablation, such as the SERF™ ablation technique (Saline Enhanced Radio Frequency™ ablation). More particularly, this invention relates to devices and methods for monitoring temperature during fluid enhanced ablation at various locations relative to an ablation element.

BACKGROUND

The use of thermal energy to destroy bodily tissue can be applied to a variety of therapeutic procedures, including the destruction of tumors. Thermal energy can be imparted to the tissue using various forms of energy, such as radio frequency electrical energy, microwave or light wave electromagnetic energy, or ultrasonic vibrational energy. Radio frequency (RF) ablation, for example, is effected by placing one or more electrodes against or into tissue to be treated and passing high frequency electrical current into the tissue. The current can flow between closely spaced emitting electrodes or between an emitting electrode and a larger, common electrode located remotely from the tissue to be heated.

One disadvantage with these techniques is that maximum heating often occurs at or near the interface between the therapeutic tool and the tissue. In RF ablation, for example, the maximum heating can occur in the tissue immediately adjacent to the emitting electrode. This can reduce the conductivity of the tissue, and in some cases, can cause water within the tissue to boil and become water vapor. As this process continues, the impedance of the tissue can increase and prevent current from entering into the surrounding tissue. Thus, conventional RF instruments are limited in the volume of tissue that can be treated.

Fluid enhanced ablation therapy, such as the SERF™ ablation technique (Saline Enhanced Radio Frequency™ ablation), can treat a greater volume of tissue than conventional RF ablation. The SERF ablation technique is described in U.S. Pat. No. 6,328,735, which is hereby incorporated by reference in its entirety. Using the SERF ablation technique, saline is passed through the needle and heated, and the heated fluid is delivered to the tissue immediately surrounding the needle. The saline helps distribute the heat developed adjacent to the needle and thereby allows a greater volume of tissue to be treated with a therapeutic dose of ablative energy. The therapy is usually completed once a target volume of tissue reaches a desired therapeutic temperature, or otherwise receives a therapeutic dose of energy.

However, it can be challenging to determine with precision when a particular targeted volume of tissue has received the desired therapeutic dose of energy. For example, Magnetic Resonance Imaging (MRI) can be used during ablation therapy to monitor the extent of the developing treatment zone, but MRI is often prohibitively costly for this type of procedure. Ultrasonic imaging can also be used, but does not reliably or accurately depict the volume of the treatment zone.

Furthermore, while fluid enhanced ablation therapy generally creates treatment zones in tissue surrounding an ablation device that are spherical in shape, anatomical features and differences in tissue types can result in non-uniform propagation of the treatment zone. Accordingly, in some cases it can be desirable to correct for a developing non-uniform treatment zone that results from anatomical features in the targeted volume of tissue (e.g., a nearby blood vessel that is moving heat away from a treatment zone). Moreover, in some situations it can be desirable to create a treatment zone having a non-standard shape. Corrective or other shaping of the developing therapy treatment zone cannot be accomplished, however, without accurate measurements of the temperature in tissue surrounding the ablation device.

Accordingly, there remains a need for devices and techniques for more accurately and reliably monitoring the temperature of tissue during fluid enhanced ablation therapy.

SUMMARY

The present invention generally provides devices and methods for monitoring the temperature of tissue at various locations within a treatment volume during fluid enhanced ablation. In one aspect, an ablation device is provided including an elongate body having a proximal end, a distal end, an inner lumen extending therethrough, and at least one outlet port configured to allow fluid flowing through the inner lumen to be delivered to tissue surrounding the elongate body when the elongate body is introduced into a tissue mass. The device further includes at least one ablation element disposed along the elongate body adjacent to the at least one outlet port, the at least one ablation element being configured to heat tissue within a treatment zone surrounding the at least one ablation element when the distal end of the elongate body is introduced into a tissue mass. The device can also include at least one temperature sensor coupled to the elongate member and positioned a distance apart from the at least one ablation element. The at least one temperature sensor is effective to output a measured temperature of tissue spaced a distance apart from tissue adjacent to the at least one ablation element such that the measured temperature indicates whether tissue is being heating to a therapeutic level.

The ablation device of the present invention can have a number of additional features and modifications. For example, the at least one temperature sensor can be positioned on the elongate body at a location proximal to the at least one ablation element. Alternatively, the at least one temperature sensor can be positioned on the elongate body at a location distal to the at least one ablation element. In other embodiments, the at least one temperature sensor can include a plurality of temperature sensors spaced apart from one another and positioned axially along the elongate body. In still other embodiments, the at least one temperature sensor can include a first temperature sensor positioned distal of the at least one ablation element, and a second temperature sensor positioned proximal of the at least one ablation element.

In some embodiments, the elongate body can include a plurality of tines configured to extend outward from the elongate body, and the at least one temperature sensor can include a plurality of temperature sensors. Each of the plurality of tines can have one of the plurality of temperature sensors located at a distal tip thereof. In other embodiments, each of the plurality of tines can have two or more of the plurality of temperature sensors disposed along a length thereof. In still other embodiments, the at least one temperature sensor can be located on an outer surface of the elongate body. Alternatively, the at least one temperature sensor can be located in the inner lumen and can contact an outer wall of the elongate body. In still other embodiments, the at least one temperature sensor can be located in a recess formed in the elongate body. In some embodiments, the at least one temperature sensor can be thermally isolated from the elongate body. In other embodiments, a position of the at least one temperature sensor can be adjustable along a length of the elongate member. In certain embodiments, the at least one temperature sensor can be a thermocouple. In other embodiments, the temperature sensor can be a wireless temperature sensor.

In another aspect, a system for delivering saline enhanced ablation is provided that includes an elongate body having proximal and distal ends, an inner lumen extending through the elongate body, at least one outlet port formed in the elongate body, and at least one ablation element positioned along the length of a distal portion of the elongate body. The system can also include a fluid source in communication with the inner lumen of the elongate body and configured to deliver fluid through the inner lumen such that fluid can flow through the at least one outlet port and be delivered to tissue surrounding the at least one ablation element. The system can further include at least one temperature sensor coupled to the elongate body and positioned a distance apart from the at least one ablation element such that the at least one temperature sensor is effective to measure a temperature of tissue spaced a distance apart from tissue adjacent to the at least one ablation element. The system can also include a control unit configured to obtain a temperature of the ablation element and a temperature measured by the at least one temperature sensor, and a temperature measured by the at least one temperature sensor can indicate whether tissue within a treatment zone is being heated to a therapeutic level.

In some embodiments, the control unit can be configured to adjust at least one of a flow rate of the fluid flowing through the elongate body, an ablative energy level of the ablation element, and a temperature of the fluid being delivered in response to a temperature measured by the at least one temperature sensor.

In another aspect, a method for ablating tissue is provided that includes inserting a needle body into a tissue mass, the needle body having an ablation element disposed thereon and at least one temperature sensor coupled thereto and effective to measure a temperature of the tissue mass at a distance away from tissue immediately adjacent to the ablation element. The method can include simultaneously delivering fluid through the needle body and into the tissue mass surrounding the needle body, and delivering therapeutic energy to the ablation element on the needle body to heat the tissue mass surrounding the needle body. The at least one temperature sensor can measure a temperature of the tissue mass at a distance away from the tissue immediately adjacent to the ablation element.

In some embodiments, the method can include adjusting at least one of a flow rate of the fluid flowing through the needle body, an ablative energy level of the ablation element, and a temperature of the fluid being delivered. In other embodiments, the tissue located a distance away from the tissue immediately adjacent to the ablation source can be at the periphery of a desired treatment zone. In another embodiment, the method can include ceasing delivery of therapeutic energy once the temperature measured by the at least one temperature sensor reaches a predetermined level. In still other embodiments, the method can include determining a therapeutic dose delivered to the tissue mass based on measurements from the at least one temperature sensor, and ceasing delivery of therapeutic energy once the thermal dose delivered to the tissue mass reaches a predetermined level.

In another aspect, a method for therapeutically treating tissue is provided that includes inserting a needle body into a tissue mass, the needle body having one or more outlet ports formed therein. The method further includes delivering fluid heated to a therapeutic temperature into the tissue mass through the one or more outlet ports to heat the tissue mass surrounding the needle body, and measuring a temperature of the tissue mass at a distance away from the tissue immediately adjacent to the one or more outlet ports. In some embodiments, measuring a temperature of the tissue mass can include detecting the temperature using a temperature sensor disposed along the length of the needle body.

BRIEF DESCRIPTION OF THE DRAWINGS

The aspects and embodiments of the invention described above will be more fully understood from the following detailed description taken in conjunction with the accompanying drawings, in which:

FIG. 9A is a cross-sectional view of one embodiment of an insulating tube configured to insulate a thermocouple from fluid flowing therethrough;

FIG. 9B is a cross-sectional view of one embodiment of an elongate body having an insulating tube disposed therein;

DETAILED DESCRIPTION

Figure 1:
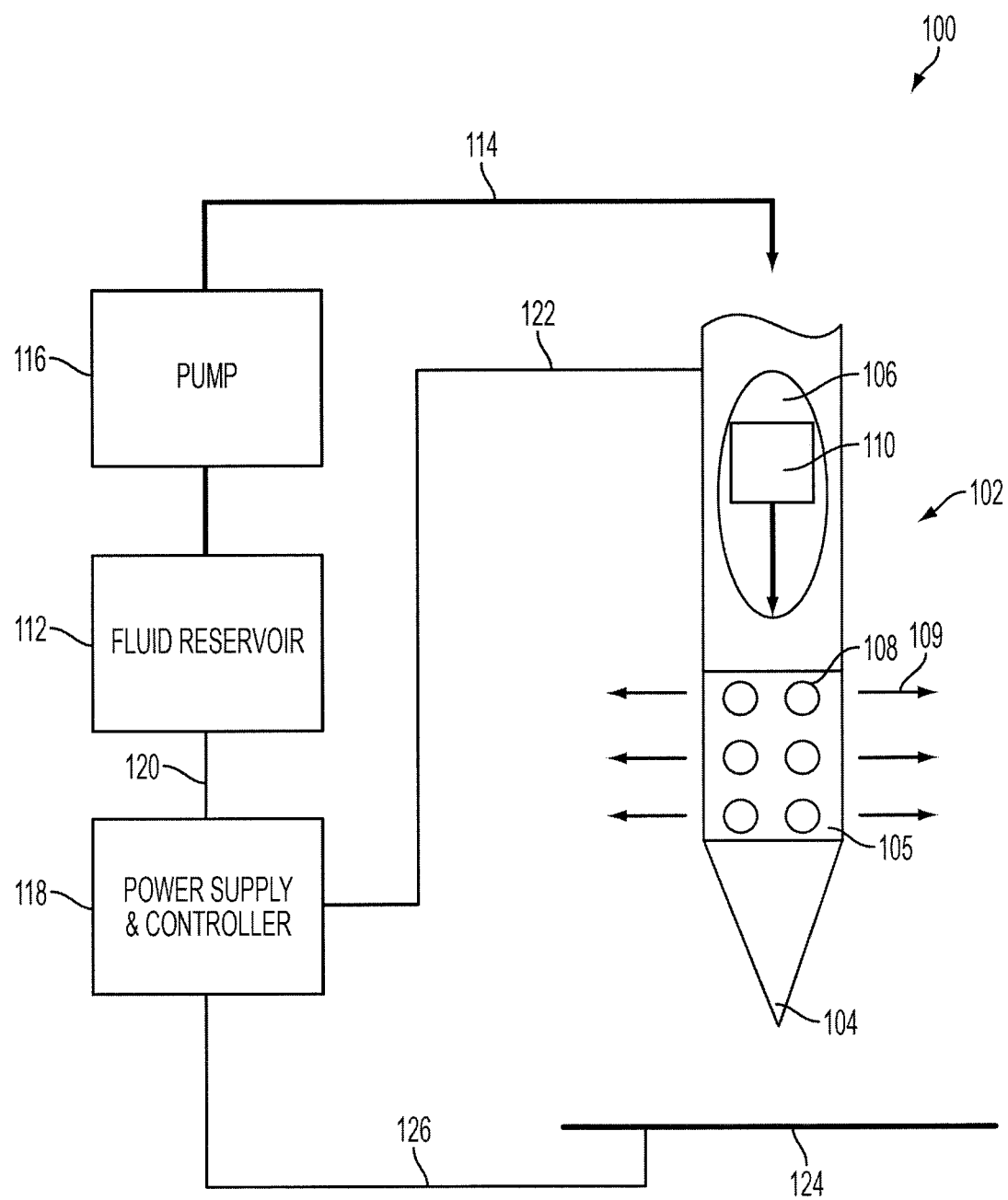
FIG. 1 is a diagram of one embodiment of a fluid enhanced ablation system.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. The terms "about" and "approximately" used for any numerical values or ranges indicate a suitable dimensional tolerance that allows the composition, part, or collection of elements to function for its intended purpose as described herein. These terms generally indicate a ±10% variation about a central value. Components described herein as being coupled may be directly coupled, or they may be indirectly coupled via one or more intermediate components. The recitation of any ranges of values herein is merely intended to serve as a shorthand method of referring individually to each separate value falling within the range, unless otherwise indicated herein, and each separate value is incorporated into the specification as if it were individually recited. Further, to the extent that linear or circular dimensions are used in the description of the disclosed devices, systems, and methods, such dimensions are not intended to limit the types of shapes that can be used in conjunction with such devices, systems, and methods. A person skilled in the art will recognize that an equivalent to such linear and circular dimensions can easily be determined for any geometric shape.

All methods described herein can be performed in any suitable order unless otherwise indicated herein or otherwise clearly contradicted by context. The use of any and all examples, or exemplary language (e.g., "such as"), provided herein is intended merely to better illuminate the invention and does not impose a limitation on the scope of the invention unless otherwise claimed. No language in the specification should be construed as indicating any non-claimed element as essential to the practice of the invention. Further, to the extent the term "saline" is used in conjunction with any embodiment herein, such embodiment is not limited to use of "saline" as opposed to another fluid unless explicitly indicated. Other fluids can typically be used in a similar manner.

Fluid Enhanced Ablation Systems

The present invention is generally directed to devices and methods for remote temperature monitoring in fluid enhanced ablation devices. Fluid enhanced ablation, as mentioned above, is defined by passing a fluid into tissue while delivering therapeutic energy from an ablation element. The delivery of therapeutic energy into tissue can cause hyperthermia in the tissue, ultimately resulting in necrosis. This temperature-induced selective destruction of tissue can be utilized to treat a variety of conditions including tumors, fibroids, cardiac dysrhythmias (e.g., ventricular tachycardia, etc.), and others.

Fluid enhanced ablation, such as the SERF™ ablation technique (Saline Enhanced Radio Frequency™ ablation) described in U.S. Pat. No. 6,328,735 and incorporated by reference above, delivers fluid heated to a therapeutic temperature into tissue along with ablative energy. Delivering heated fluid enhances the ablation treatment because the fluid flow through the extracellular space of the treatment tissue can increase the heat transfer through the tissue by more than a factor of twenty. The flowing heated fluid convects thermal energy from the ablation energy source further into the target tissue. In addition, the fact that the fluid is heated to a therapeutic temperature increases the amount of energy that can be imparted into the tissue. Finally, the fluid can also serve to constantly hydrate the tissue and prevent any charring and associated impedance rise.

Figure 2:
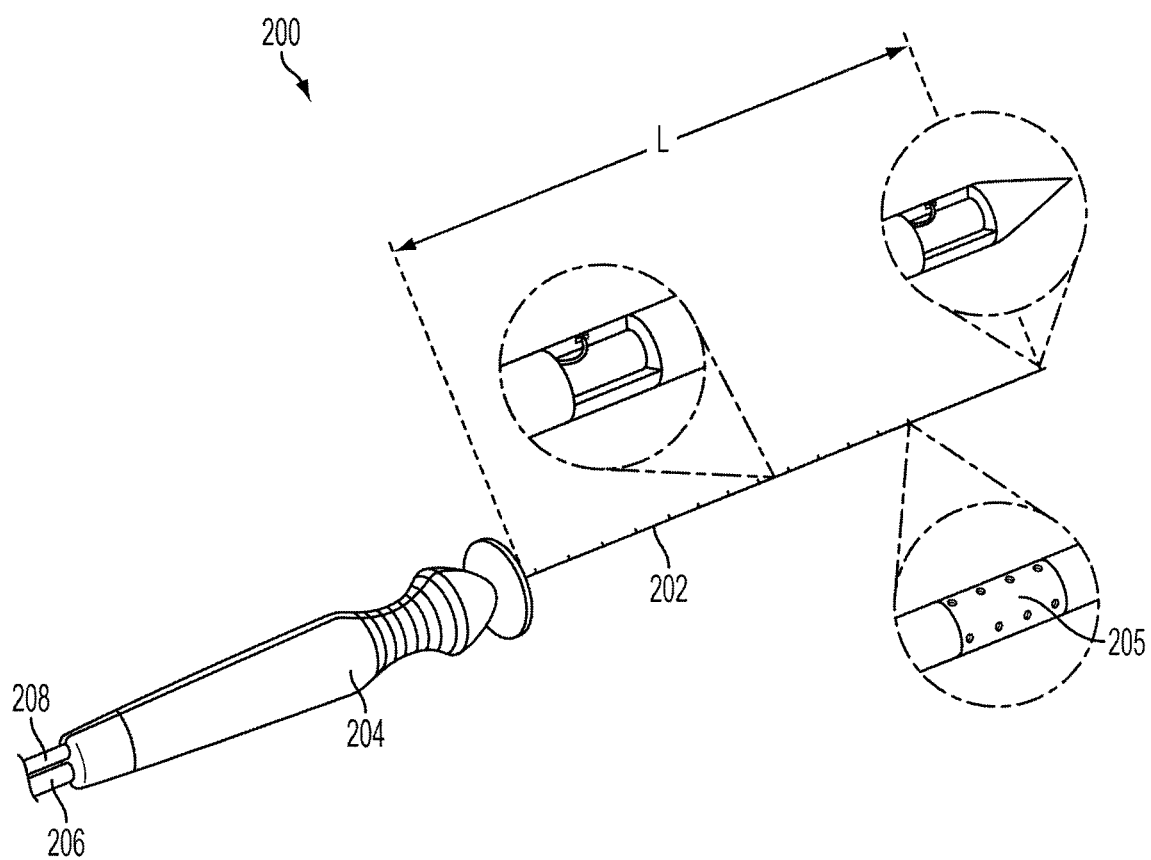
FIG. 2 is a perspective view of one embodiment of a medical device having an elongate body for use in fluid enhanced ablation.

FIG. 1 illustrates a diagram of one exemplary fluid ablation system 100. The system includes an elongate body 102 configured for insertion into a target volume of tissue. The elongate body can have a variety of shapes and sizes according to the geometry of the target tissue. Further, the particular size of the elongate body can depend on a variety of factors including the type and location of tissue to be treated, the size of the tissue volume to be treated, etc. By way of example only, in one embodiment, the elongate body can be a thin-walled stainless steel needle between about 16- and about 18-gauge (i.e., an outer diameter of about 1.27 millimeters to about 1.65 millimeters), and having a length L (e.g., as shown in FIG. 2) that is approximately 25 cm. The elongate body 102 can include a pointed distal tip 104 configured to puncture tissue to facilitate introduction of the device into a target volume of tissue, however, in other embodiments the tip can be blunt and can have various other configurations. The elongate body 102 can be formed from a conductive material such that the elongate body can conduct electrical energy along its length to one or more ablation elements located along a distal portion of the elongate body. Emitter electrode 105 is an example of an ablation element capable of delivering RF energy from the elongate body.

In some embodiments, the emitter electrode 105 can be a portion of the elongate body 102. For example, the elongate body 102 can be coated in an insulating material along its entire length except for the portion representing the emitter electrode 105. More particularly, in one embodiment, the elongate body 102 can be coated in 1.5 mil of the fluoropolymer Xylan™ 8840. The electrode 105 can have a variety of lengths and shape configurations. In one embodiment, the electrode 105 can be a 4 mm section of a tubular elongate body that is exposed to surrounding tissue. Further, the electrode 105 can be located anywhere along the length of the elongate body 105 (and there can also be more than one electrode disposed along the length of the elongate body). In one embodiment, the electrode can be located adjacent to the distal tip 104. In other embodiments, the elongate body can be formed from an insulating material, and the electrode can be disposed around the elongate body or between portions of the elongate body.

In other embodiments, the electrode can be formed from a variety of other materials suitable for conducting current. Any metal or metal salt may be used. Aside from stainless steel, exemplary metals include platinum, gold, or silver, and exemplary metal salts include silver/silver chloride. In one embodiment, the electrode can be formed from silver/silver chloride. It is known that metal electrodes assume a voltage potential different from that of surrounding tissue and/or liquid. Passing a current through this voltage difference can result in energy dissipation at the electrode/tissue interface, which can exacerbate excessive heating of the tissue near the electrodes. One advantage of using a metal salt such as silver/silver chloride is that it has a high exchange current density. As a result, a large amount of current can be passed through such an electrode into tissue with only a small voltage drop, thereby minimizing energy dissipation at this interface. Thus, an electrode formed from a metal salt such as silver/silver chloride can reduce excessive energy generation at the tissue interface and thereby produce a more desirable therapeutic temperature profile, even where there is no liquid flow about the electrode.

The electrode 105 or other ablation element can include one or more outlet ports 108 that are configured to deliver fluid from an inner lumen 106 extending through the elongate body 102 into surrounding tissue (as shown by arrows 109). Alternatively, the electrode 105 can be positioned near one or more outlet ports 108 formed in the elongate body 102. In many embodiments, it can be desirable to position the electrode adjacent to the one or more outlet ports 108 to maximize the effect of the flowing fluid on the therapy. The outlet ports 108 can be formed in a variety of sizes, numbers, and pattern configurations. In addition, the outlet ports 108 can be configured to direct fluid in a variety of directions with respect to the elongate body 102. These can include the normal orientation (i.e., perpendicular to the elongate body surface) shown by arrows 109 in FIG. 1, as well as orientations directed proximally and distally along a longitudinal axis of the elongate body 102, including various orientations that develop a circular or spiral flow of liquid around the elongate body. Still further, in some embodiments, the elongate body 102 can be formed with an open distal end that serves as an outlet port. By way of example, in one embodiment, twenty-four equally-spaced outlet ports 108 having a diameter of about 0.4 mm can be created around the circumference of the electrode 105 using Electrical Discharge Machining (EDM). One skilled in the art will appreciate that additional manufacturing methods are available to create the outlet ports 108. In addition, in some embodiments, the outlet ports can be disposed along a portion of the elongate body adjacent to the electrode, rather than being disposed in the electrode itself.

The inner lumen 106 that communicates with the outlet ports 108 can also house a heating assembly 110 configured to heat fluid as it passes through the inner lumen 106 just prior to being introduced into tissue. Detailed discussion of various embodiments of the heating assembly 110 suitable for use in devices and methods of the present invention can be found in related U.S. application Ser. No. 13/445,036, issued as U.S. Pat. No. 9,138,287, entitled "Methods and Devices for Heating Fluid in Fluid Enhanced Ablation Therapy," filed concurrently with the present application and incorporated by reference in its entirety above.

The portion of the elongate body located distal to the electrode 105 or other ablation element can be solid or filled such that the inner lumen 106 terminates at the distal end of the electrode 105. In one embodiment, the inner volume of the portion of the elongate body distal to the electrode can be filled with a plastic plug that can be epoxied in place or held by an interference fit. In other embodiments, the portion of the elongate body distal to the electrode can be formed from solid metal and attached to the proximal portion of the elongate body by welding, swaging, or any other technique known in the art.

Fluid can be supplied to the inner lumen 106 and heating assembly 110 from a fluid reservoir 112. The fluid reservoir 112 can be connected to the inner lumen 106 via a fluid conduit 114. The fluid conduit 114 can be, for example, a length of flexible plastic tubing. The fluid conduit 114 can also be a rigid tube, or a combination of rigid and flexible tubing.

Fluid can be urged from the fluid reservoir 112 into the inner lumen 106 by a pump 116. The pump 116 can be a syringe-type pump that produces a fixed volume flow with advancement of a plunger (not shown). An example of such a pump is a Model 74900 sold by Cole-Palmer Corporation of Chicago, Ill. Other types of pumps, such as a diaphragm pump, may also be employed.

The pump 116 can be controlled by a power supply and controller 118. The power supply and controller 118 can deliver electrical control signals to the pump 116 to cause the pump to produce a desired flow rate of fluid. The power supply and controller 118 can be connected to the pump 116 via an electrical connection 120. The power supply and controller 118 can also be electrically connected to the elongate body 102 via connection 122, and to a collector electrode 124 via connection 126. In addition, the power supply and controller 118 can be connected to the heating assembly 110 through a similar electrical connection.

The collector electrode 124 can have a variety of forms. For example, the collector electrode 124 can be a large electrode located outside a patient's body. In other embodiments, the collector electrode 124 can be a return electrode located elsewhere along the elongate body 102, or it can be located on a second elongate body introduced into a patient's body near the treatment site.

In operation, the power supply and controller 118 can drive the delivery of fluid into target tissue at a desired flow rate, the heating of the fluid to a desired therapeutic temperature, and the delivery of therapeutic ablative energy via the one or more ablation elements, such as electrode 105. To do so, the power supply and controller 118 can itself comprise a number of components for generating, regulating, and delivering required electrical control and therapeutic energy signals. For example, the power supply and controller 118 can include one or more frequency generators to create one or more RF signals of a given amplitude and frequency. These signals can be amplified by one or more RF power amplifiers into relatively high-voltage, high-amperage signals, e.g., 50 volts at 1 amp. These RF signals can be delivered to the ablation element via one or more electrical connections 122 and the elongate body 102 such that RF energy is passed between the emitter electrode 105 and the collector electrode 124 that can be located remotely on a patient's body. In embodiments in which the elongate body is formed from non-conductive material, the one or more electrical connections 122 can extend through the inner lumen of the elongate body or along its outer surface to deliver current to the emitter electrode 105. The passage of RF energy between the ablation element and the collector electrode 124 can heat the tissue surrounding the elongate body 102 due to the inherent electrical resistivity of the tissue. The power supply and controller 118 can also include a directional coupler to feed a portion of the one or more RF signals to, for example, a power monitor to permit adjustment of the RF signal power to a desired treatment level.

The elongate body 102 illustrated in FIG. 1 can be configured for insertion into a patient's body in a variety of manners. FIG. 2 illustrates one embodiment of a medical device 200 having an elongate body 202 disposed on a distal end thereof configured for laparoscopic or direct insertion into a target area of tissue. In addition to the elongate body 202, the device 200 can include a handle 204 to allow an operator to manipulate the device. The handle 204 can include one or more electrical connections 206 that connect various components of the elongate body (e.g., the heating assembly and ablation element 205) to, for example, the power supply and controller 118 described above. The handle 204 can also include at least one fluid conduit 208 for connecting a fluid source to the device 200.

While device 200 is one exemplary embodiment of a medical device that can be adapted for use in fluid enhanced ablation, a number of other devices can also be employed. For example, a very small elongate body can be required in treating cardiac dysrhythmias, such as ventricular tachycardia. In such a case, an appropriately sized elongate body can be, for example, disposed at a distal end of a catheter configured for insertion into the heart via the circulatory system. In one embodiment, a stainless steel needle body between about 20- and about 25-gauge (i.e., an outer diameter of about 0.5 millimeters to about 0.9 millimeters) can be disposed at a distal end of a catheter. The catheter can have a variety of sizes but, in some embodiments, it can have a length of about 120 cm and a diameter of about 8 French ("French" is a unit of measure used in the catheter industry to describe the size of a catheter and is equal to three times the diameter of the catheter in millimeters).

Therapeutic Treatment Using Fluid Enhanced Ablation

Ablation generally involves the application of high or low temperatures to cause the selective necrosis and/or removal of tissue. There is a known time-temperature relationship in the thermal destruction of tissue accomplished by ablation. A threshold temperature for causing irreversible thermal damage to tissue is generally accepted to be about 41° Celsius (C). It is also known that the time required to achieve a particular level of cell necrosis decreases as the treatment temperature increases further above 41° C. It is understood that the exact time/temperature relationship varies by cell type, but that there is a general relationship across many cell types that can be used to determine a desired thermal dose level. This relationship is commonly referred to as an equivalent time at 43° C. expressed as:

$$t_{eq,43°\ C.} = \int R^{(T(t)-43°)} dt \qquad (1)$$

where T is the tissue temperature and R is a unit-less indicator of therapeutic efficiency in a range between 0 and 5 (typically 2 for temperatures greater than or equal to 43° C., zero for temperatures below 41° C., and 4 for temperatures between 41 and 43° C.), as described in Sapareto S. A. and W. C. Dewey, *Int. J. Rad. Onc. Biol. Phys.* 10(6):787-800 (1984). This equation and parameter set represents just one example of the many known methods for computing a thermal dose, and any of methodology can be employed with the methods and devices of the present invention. Using equation (1) above, thermal doses in the range of $t_{eq,43°\ C.}$=20 minutes to 1 hour are generally accepted as therapeutic although there is some thought that the dose required to kill tissue is dependent on the type of tissue. Thus, therapeutic temperature may refer to any temperature in excess of 41° C., but the delivered dose and, ultimately, the therapeutic effect are determined by the temporal history of temperature (i.e., the amount of heating the tissue has previously endured), the type of tissue being heated, and equation (1). For example, Nath, S. and Haines, D. E., *Prog. Card. Dis.* 37(4):185-205 (1995) (Nath et al.) suggest a temperature of 50° C. for one minute as therapeutic, which is an equivalent time at 43° C. of 128 minutes with R=2. In addition, for maximum efficiency, the therapeutic temperature should be uniform throughout the tissue being treated so that the thermal dose is uniformly delivered.

Figure 3:
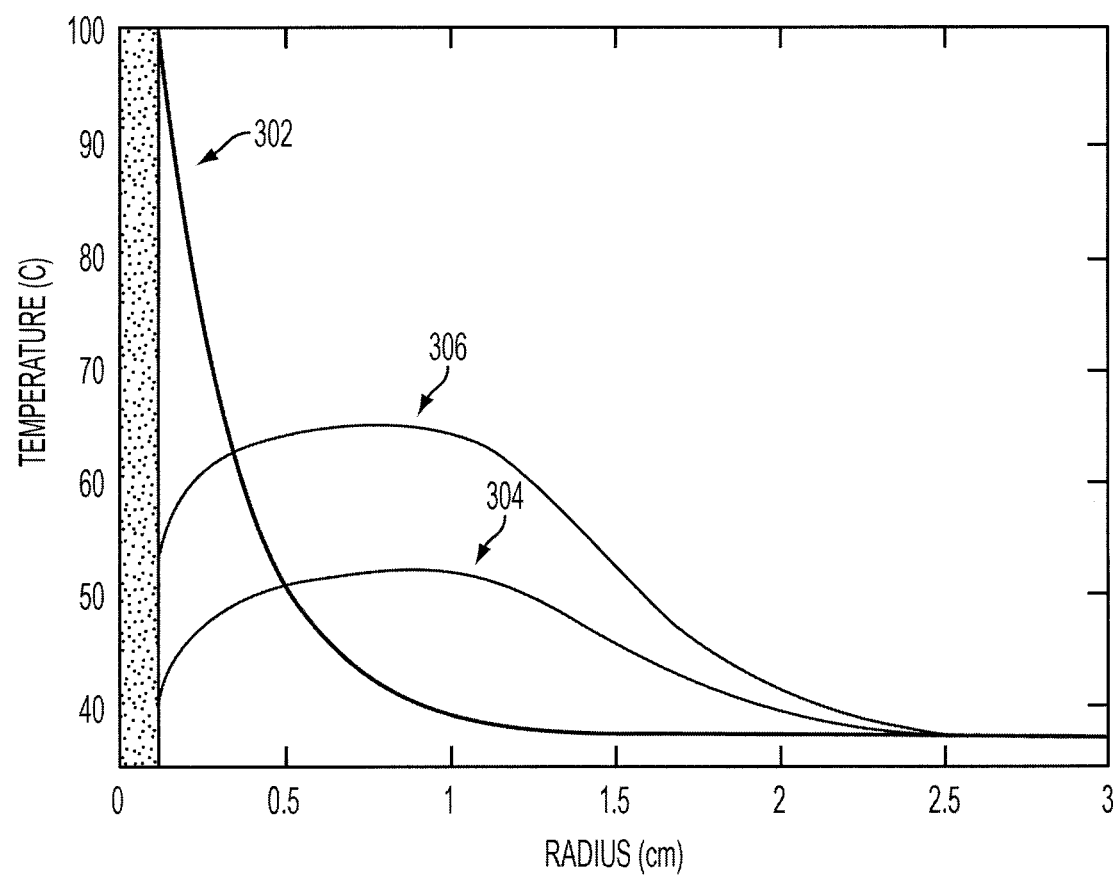
FIG. 3 is a graphical representation of simulated heating profiles for various forms of ablation.

FIG. 3 illustrates the performance profiles of several ablation techniques by showing a simulated temperature achieved at a given distance from an ablation element, such as electrode 105. The first profile 302 illustrates the performance of RF ablation without the use of fluid enhancement. As shown in the figure, the temperature of the tissue falls very sharply with distance from the electrode. This means that within 10 millimeters of the ablation element the temperature of the tissue is still approximately body temperature (37° C.), far below the therapeutic temperature of 50° C. discussed above. Furthermore, very close to the ablation element the temperature is very high, meaning that the tissue will more quickly desiccate, or dry up, and char. Once this happens, the impedance of the tissue rises dramatically, making it difficult to pass energy to tissue farther away from the ablation element.

A second tissue temperature profile 304 is associated with a second prior art system similar to that described in U.S. Pat. No. 5,431,649. In this second system, an electrode is inserted into tissue and imparts a 400 kHz RF current flow of about 525 mA to heat the tissue. Body temperature (37° C.) saline solution is simultaneously injected into the tissue at a rate of 10 ml/min. The resulting tissue temperature profile 304 is more uniform than profile 302, but the maximum temperature achieved anywhere is approximately 50° C. Thus, the temperature profile 304 exceeds the generally accepted tissue damaging temperature threshold specified for one minute of therapy in only a small portion of the tissue. As described above, such a small temperature increment requires significant treatment time to achieve any therapeutically meaningful results.

A third tissue temperature profile 306 is achieved using the teachings of the present invention. In the illustrated embodiment, an electrode formed from silver/silver chloride is inserted into tissue and imparts a 480 kHz RF current flow of 525 mA to heat the tissue. Saline solution heated to 50° C. is simultaneously injected into the tissue at a rate of 10 ml/min. The resulting temperature profile 306 is both uniform and significantly above the 50° C. therapeutic threshold out to 15 millimeters from the electrode. Moreover, because the temperature is uniform within this volume, the thermal dose delivered is also uniform through this volume.

The uniform temperature profile seen in FIG. 3 can be achieved by the introduction of heated fluid into the target tissue during application of ablative energy. The fluid convects the heat deeper into the tissue, thereby reducing the charring and impedance change in tissue that occurs near the ablation element, as shown in profile 302. Further, because the fluid is heated to a therapeutic level, it does not act as a heat sink that draws down the temperature of the surrounding tissue, as seen in profile 304. Therefore, the concurrent application of RF energy and perfusion of heated saline solution into the tissue eliminates the desiccation and/or vaporization of tissue adjacent to the electrode, maintains the effective tissue impedance, and increases the thermal transport within the tissue being heated with RF energy. The total volume of tissue that can be heated to therapeutic temperatures, e.g., greater than 41° C., is thereby increased. For example, experimental testing has demonstrated that a volume of tissue having a diameter of approximately 8 centimeters (i.e., a spherical volume of approximately 156 cm$^3$) can be treated in 5 minutes using the fluid enhanced ablation techniques described herein. By comparison, conventional RF can only treat volumes having a diameter of approximately 3 centimeters (i.e., a spherical volume of approximately 14 cm$^3$) in the same 5-minute time span.

In addition, fluid enhanced ablation devices according to the present invention have a greater number of parameters that can be varied to adjust the shape of the treatment profile according to the tissue being treated. For example, when using the SERF ablation technique, an operator or control system can modify parameters such as saline temperature (e.g., from about 40° C. to about 80° C.), saline flow rate (e.g., from about 0 ml/min to about 20 ml/min), RF signal power (e.g., from about 0 W to about 100 W), and duration of treatment (e.g., from about 0 minutes to about 10 minutes) to adjust the temperature profile 306. In addition, different electrode configurations can also be used to vary the treatment. For example, although the emitter electrode 105 illustrated in FIG. 1 is configured as a continuous cylindrical band adapted for a mono-polar current flow, the electrode can also be formed in other geometries, such as spherical or helical, that form a continuous surface area, or the electrode may have a plurality of discrete portions. The electrodes may also be configured for bipolar operation, in which one electrode (or a portion of an electrode) acts as a cathode and another electrode (or portion thereof) acts as an anode.

A preferred fluid for use in the SERF ablation technique is sterile normal saline solution (defined as a salt-containing solution). However, other liquids may be used, including Ringer's solution, or concentrated saline solution. A fluid can be selected to provide the desired therapeutic and physical properties when applied to the target tissue and a sterile fluid is recommended to guard against infection of the tissue.

Treatment Zone Development and Monitoring

In fluid enhanced ablation therapy, ablative energy generally expands from an ablation element, such as emitter electrode 105, in a roughly spherical pattern. This, in turn, creates ablation therapy treatment zones, volumes, or regions (i.e., regions that receive a therapeutic dose of ablative energy by reaching a therapeutic temperature for a period of time, as discussed above) that have a roughly spherical shape. The diameter of the spherical treatment zone can increase as the treatment time is lengthened.

Figure 4:
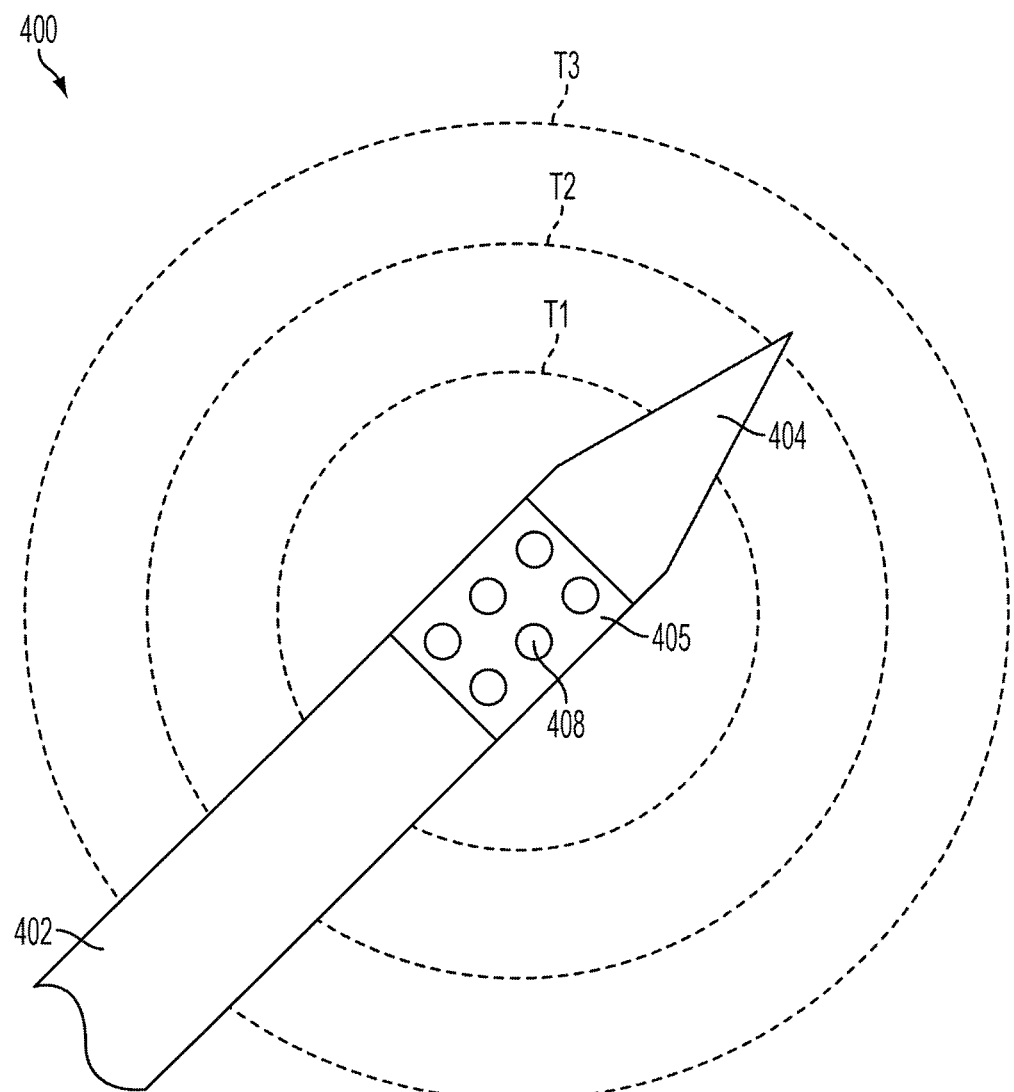
FIG. 4 is a side view of a distal portion of an elongate body showing the expansion of a treatment zone over time.

One embodiment of this behavior is illustrated in FIG. 4. The figure shows one embodiment of an ablation device 400 that includes an elongate body 402 having a distal tip 404 and an emitter electrode 405. A plurality of outlet ports 408 can be positioned along an outer surface of the emitter electrode 405 and can be configured to deliver fluid into the tissue surrounding the elongate body 402. As heated fluid is delivered from the outlet ports 408 and ablative energy is delivered into the tissue via the emitter electrode 405, a treatment zone develops at a first time that is defined by the dotted lines labeled $T_1$. While drawn as a two-dimensional circle, one skilled in the art will appreciate that the treatment zone represented is roughly spherical in shape. As the treatment time increases, so too does the diameter of the treatment zone, until it reaches the dotted lines labeled $T_2$ at a second time that is greater than the first time. Similarly, at a third time greater than the second time, the treatment zone can reach the dotted lines labeled $T_3$.

The propagation of the treatment zone over time can be affected by a variety of factors. These can include factors related to the tissue being treated (e.g., features, tissue type, amount of heating already endured, etc.) as well as factors related to the therapy operating parameters (e.g. temperature of fluid being delivered, flow rate of fluid being delivered, level of ablative energy being delivered, etc.). As mentioned above, fluid enhanced ablation has a greater number of tunable operating parameters than conventional ablation therapy techniques, and all of these can affect the development of the treatment zone.

Figure 5:
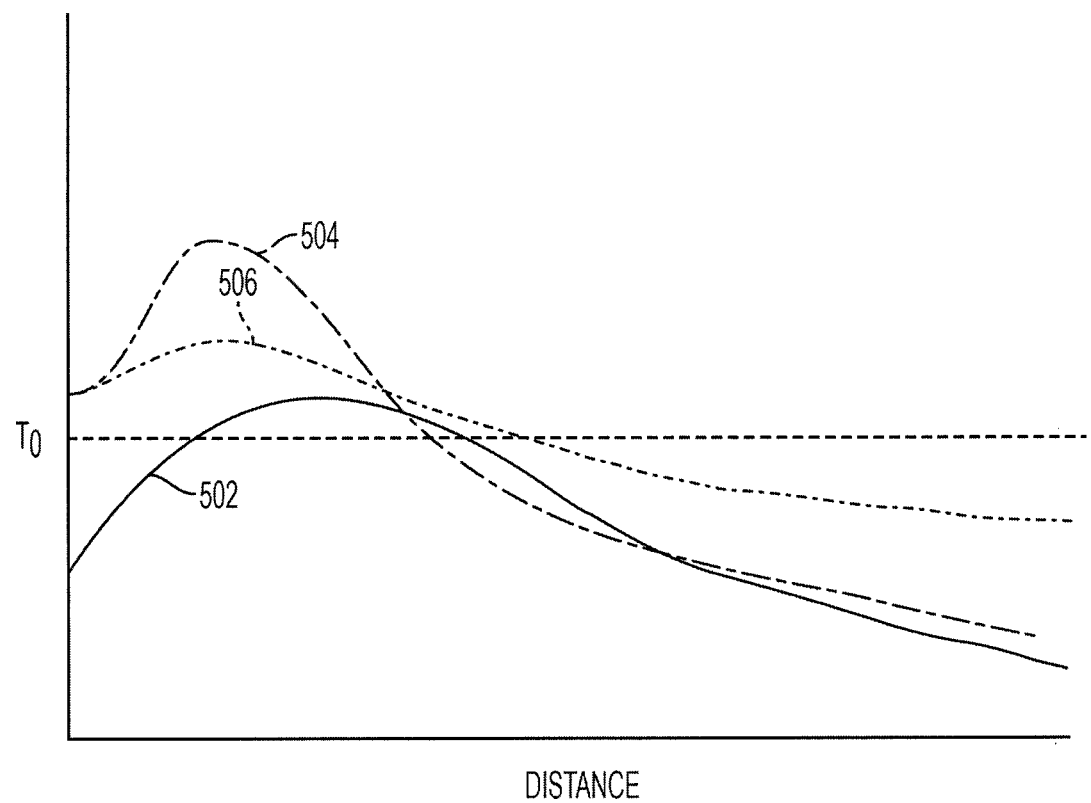
FIG. 5 is a graphical representation of variation in heating profiles during fluid enhanced ablation.

FIG. 5 illustrates a few examples of treatment profiles that can be achieved by adjusting various operating parameters of the fluid enhanced ablation system. For example, if a volume of tissue is to be treated with fluid enhanced ablation at a therapeutic temperature of $T_0$ for a period of time, initial operating parameters may produce an initial treatment profile 502. As shown in the figure, the treatment profile 502 does not bring tissue located a distance away from the ablation element above the therapeutic temperature. To tune the system, an operator or control system can, for example, increase the ablative energy level being applied to the tissue. This can result in the second treatment profile 504. The second treatment profile 504 delivers therapeutic heat farther into tissue, but also delivers significantly more heat into tissue located closer to the ablation element. This additional heat may be undesirable and can lead to charring of the tissue. In response, the operator or control system can further adjust the operating parameters of the system by, for example, increasing the flow rate of therapeutically heated saline being introduced into the tissue at or immediately adjacent to the ablative element. Doing so can have the effect of smoothing out the temperature spike seen in the treatment profile 504, producing the treatment profile 506. This treatment profile brings tissue to a therapeutic temperature over the largest distance from the ablation element and avoids an undesirable temperature spike closer to the ablation element.

It is often desirable to produce the most uniform treatment profile possible within the treatment volume wherein all portions of the volume receive the same therapeutic dose of ablative energy. In FIG. 5, such a treatment profile can be shown by a horizontal line across the depth of the treatment zone. Fluid enhanced ablation approximates this ideal scenario far more closely than other ablation techniques because it more effectively distributes thermal energy into tissue and provides more flexibility in shaping the treatment profile to accommodate variations due to operating parameters or anatomical features or properties.

However, in order to provide for effective tuning of fluid enhanced ablation operating parameters, it can be desirable to gather feedback regarding the temperature of tissue at various locations throughout a targeted treatment volume. In U.S. Pat. No. 6,328,735 incorporated by reference above, an elongate body for use in fluid enhanced ablation is disclosed having a single temperature sensor located immediately adjacent to the ablation element (i.e., the emitter electrode).

This sensor location, however, does not report the temperature of tissue at locations a distance apart, i.e., remote, from the ablation element.

Accordingly, fluid enhanced ablation systems can include one or more temperature sensors that are introduced at various locations a distance apart from the ablation element to provide a more accurate assessment of the propagation of the thermal energy being delivered into tissue, thereby allowing a more accurate calculation of the therapeutic dosage and more control over the ablation therapy generally.

Figure 6:
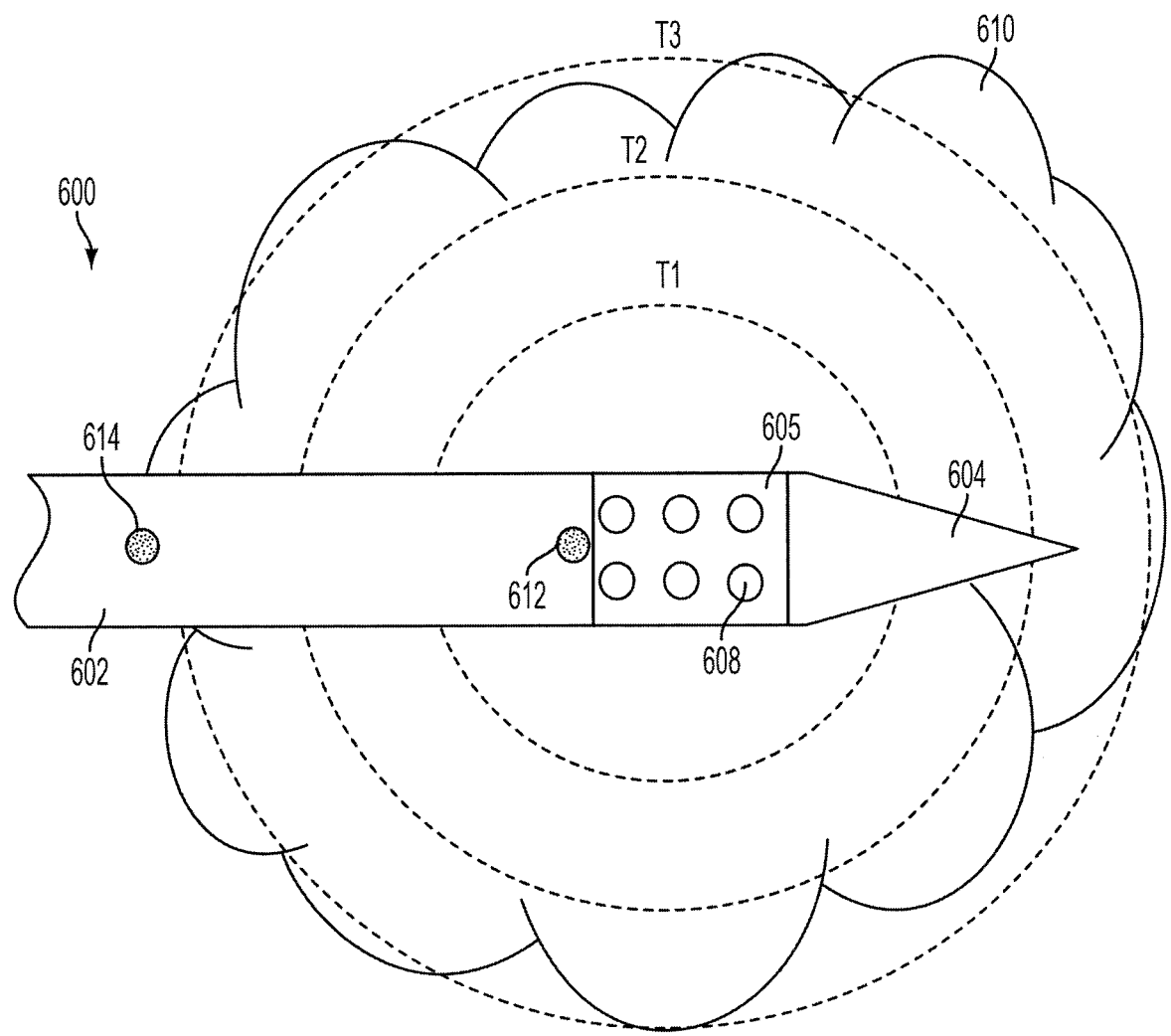
FIG. 6 is a side view of a distal portion of an elongate body having a temperature sensor located remotely from an ablation element.

One embodiment of a fluid enhanced ablation device having an additional temperature sensor is illustrated in FIG. 6. As shown, the device 600 includes an elongate body 602 having an inner lumen (not shown) extending therethrough. The elongate body 602 can have a pointed distal tip 604 to facilitate entry into tissue, though other shapes can be used, as described above. The elongate body 602 also includes an ablation element 605 having one or more outlet ports 608 formed therein that are in fluid communication with the inner lumen extending through the elongate body 602.

In use, the elongate body 602 can be inserted into a lesion 610 or other targeted volume of tissue and positioned such that the ablation element 605 is located substantially in the center of the lesion 610. Ablative energy and heated fluid can then be delivered simultaneously into the surrounding tissue to begin therapy (in some embodiments, however, the delivery of heated fluid alone can produce the desired therapeutic result). The dotted lines $T_1$, $T_2$, $T_3$ indicate the portion of the lesion that receives a therapeutic dose of ablative energy at times $T_1$, $T_2$, $T_3$, where $T_3$ is greater than $T_2$, and $T_2$ is greater than $T_1$.

The elongate body 602 also includes two temperature sensors located along the length of the elongate body to measure the temperature of adjacent tissue. A first temperature sensor 612 can be located immediately adjacent to the ablation element 605 in either a proximal or distal direction. The second temperature sensor 614, by contrast, can be located a distance apart from the ablation element 605 along the length of the elongate body 602. The second temperature sensor 614 can thus be configured to measure the temperature of adjacent tissue that is located a distance away from the ablation element 605 and from the tissue immediately adjacent to the ablation element. In some embodiments, the location of the second temperature sensor 614 can be selected such that the second temperature sensor is positioned at the edge of the desired treatment zone (e.g., lesion 610). In other embodiments, however, the second temperature sensor 614 can be positioned at a location between the ablation element and the edge of the desired treatment zone. In certain embodiments, the second temperature sensor 614 can be positioned at least about 5 mm from the ablation element 605 so that the temperature measurement from the second temperature sensor remains distinct from the measurement of the first temperature sensor 612.

Moreover, the second temperature sensor 614 can be positioned at a location proximal or distal to the ablation element. In some embodiments, however, it can be preferable to position the second temperature sensor 614 proximal to the ablation element 605, as doing so requires a shallower insertion of the elongate body 602 into tissue. For example, if the second temperature sensor 614 is located distal to the ablation element 605, the elongate body 602 must be inserted into, for example, the lesion 610 to a depth greater than the configuration shown in FIG. 6 so that the ablation element 605 is positioned at the center of the lesion 610 and the second temperature sensor 614 is positioned near the periphery of the lesion opposite from its illustrated position in the figure.

As mentioned above, in some embodiments the second temperature sensor 614 can be positioned such that it is located near the periphery of the targeted treatment volume, as shown in FIG. 6. This configuration can be advantageous because the second temperature sensor 614 can be used to provide an indication that therapy can be terminated. That is, once a temperature sensor located at the periphery of a targeted treatment volume indicates that a therapeutic dose of energy has been delivered at the periphery (e.g., a threshold temperature is reached for a given amount of time), an operator or control system can terminate the ablation therapy. In other embodiments, the temperature measured by the second temperature sensor 614 can be compared to the temperature measured by the first temperature sensor 612 to determine if the treatment volume has received a therapeutic dose of ablative energy.

Placing the second temperature sensor 614 at the periphery of a targeted treatment volume, such as lesion 610, can be accomplished in a variety of manners. For example, the targeted treatment volume can be imaged in advance of ablation therapy using any number of medical imaging technologies such as ultrasound, Magnetic Resonance Imaging (MRI), etc. Following imaging, an operator can select an appropriately sized elongate body having a distance between the first and second temperature sensors 612, 614 that is approximately equal to half the diameter of the targeted volume or lesion 610. Alternatively, and as is explained in more detail below, the second temperature sensor 614 can be configured to slide or otherwise adjust along the length of the elongate body 602. In such an embodiment, the position of the second temperature sensor 614 can be adjusted following a determination, via medical imaging or other measurement technology, of the size of the targeted treatment volume.

In other embodiments, a plurality of additional temperature sensors can be placed along the length of the elongate body to provide more detailed and precise feedback regarding the heating of tissue surrounding the elongate body. This can be accomplished, for example, by placing a plurality of temperature sensors in a line extending proximally from the first temperature sensor 612 to the second temperature sensor 614. One skilled in the art will appreciate that the additional temperature sensors can provide additional observation points that allow more precise tracking of the propagation of thermal energy from the ablation element 605.

Figure 7:
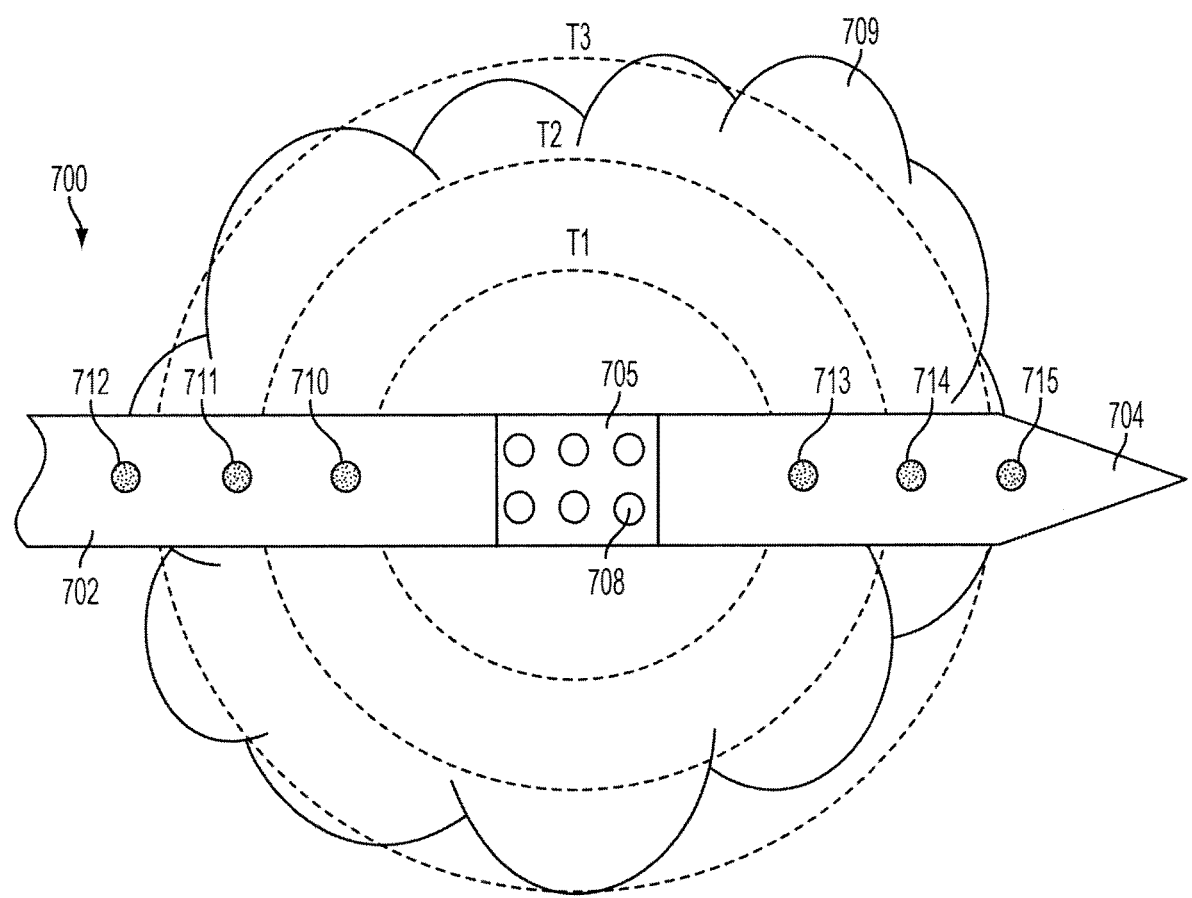
FIG. 7 is a side view of a distal portion of an elongate body having a plurality of temperature sensors located remotely from an ablation element.

The concepts described above regarding the placement of one or more additional temperature sensors along the elongate body at locations proximal and remote from the ablation element can also be applied in the distal direction. FIG. 7 illustrates one embodiment of a fluid enhanced ablation device having remotely located temperature sensors positioned both proximally and distally from an ablation element. Similar to the devices described above, the device 700 can include an elongate body 702 having a proximal end and a distal tip 704, as well as an ablation element 705 (e.g., an emitter electrode) with one or more outlet ports 708 formed therein to allow fluid to pass from an inner lumen of the elongate body 702 into surrounding tissue.

In addition, the elongate body can include a plurality of temperature sensors including first, second, and third proximal temperature sensors 710, 711, 712 positioned proximal of the ablation element 705. The first temperature sensor 710 can be located a first distance away from the ablation element 705. The second temperature sensor 711 can be located a second distance away from the ablation element 705 that is greater than the first distance. Similarly, the third temperature sensor 712 can be located a third distance away from the ablation element 705 that is greater than the second distance.

In a symmetrical arrangement, the elongate body can also include first, second, and third distal temperature sensors 713, 714, 715 positioned distal of the ablation element 705 in a similar spacing arrangement as temperature sensors 710, 711, 712. The end result is a fluid enhanced ablation device capable of measuring temperature along a longitudinal axis of the elongate body at a variety of locations on either side of an ablation element to accurately map the temperature of tissue surrounding the elongate body.

As shown in the figure, the plurality of temperature sensors can be positioned in a single line, e.g., extending along a longitudinal axis of the elongate body. In other embodiments, however, the temperature sensors can be positioned at various locations around the circumference of the elongate body, thereby forming a corkscrew or spiral pattern. Furthermore, the elongate body can include additional lines of temperature sensors similar to the sensors shown in FIG. 7, each of which can be positioned at a different location around the circumference of the elongate body. These additional temperature sensors can provide still greater detail of the temperature in the tissue surrounding the elongate body 702.

In use, the device illustrated in FIG. 7 can be positioned in a treatment volume (e.g., lesion 709) such that the ablation element 705 is located approximately in the center of the volume. The first, second, and third proximal temperature sensors 710, 711, 712 can be positioned symmetrically with respect to the first, second, and third distal temperature sensors 713, 714, 715. Similar to the embodiments described above, the size of the elongate body 702 and the spacing of the temperature sensors along the elongate body can be selected according to the size of the lesion 709, which can be imaged before ablation therapy using any of the medical imaging technologies discussed above or otherwise known in the art.

After the elongate body 702 is positioned within the lesion 709, therapy can begin by delivering therapeutically heated saline alone or in combination with ablative energy from the ablation element 705. A control system or operator can monitor the readouts from the plurality of temperature sensors to determine the extent of the therapeutic treatment volume. For example, at a first time $T_1$ the operator or control system can detect a therapeutic temperature from the first proximal and distal temperature sensors 710, 713, but not from any of the other temperature sensors. This can indicate that the volume shown by the dotted lines $T_1$ has received a therapeutic dose of ablative energy. Similarly, at a time $T_2$ that is greater than $T_1$, the second proximal and distal temperature sensors 711, 714 can detect a therapeutic temperature as the treatment region expands to the dotted lines $T_2$. Finally, at a third time $T_3$ greater than the second time $T_2$, the third proximal and distal temperature sensors 712, 715 can detect a therapeutic temperature, thereby indicating that the region represented by the dotted lines $T_3$ has received a therapeutic dose of ablative energy. As with the previous embodiments, the location of the third proximal and distal temperature sensors 712, 715 can be selected such that the sensors are located on the periphery of a desired treatment volume, such as the lesion 709 shown in the figure. This can be done using, for example, ultrasound, MRI, or other imaging technologies. In addition, any of the illustrated proximal temperature sensors 710, 711, 712 or the distal sensors 713, 714, 715 can detect a temperature in any order and at any time. Any particular sensor can detect a temperature at a same time or a different time than any other temperature sensor at any time throughout the therapy.

In other embodiments, the device 700 can be configured such that the most proximal and most distal temperature sensors (e.g., sensors 712, 715) are positioned outside of the desired treatment volume (e.g., lesion 709) while an inner set of temperature sensors (e.g., sensors 711, 714) are positioned at the edge of the treatment volume and one or more additional temperature sensors (e.g., sensors 710, 713) are within the treatment volume. In such a configuration, the temperature sensors located at the edge of the treatment volume can indicate when therapy is complete, while the inner temperature sensors can monitor the uniformity of temperature within the treatment volume and the temperature sensors positioned outside of the treatment volume can ensure that adjacent tissue does not receive a therapeutic dose of heat.

The devices described above can be formed in a variety of sizes suitable to provide therapy to a wide range of lesions. By way of example only, lesions ranging from 5 mm to 100 mm have been treated using the devices disclosed herein. One skilled in the art will appreciate that the spacing between any temperature sensors included in a device can depend on the size of the device and the size of the lesion or other target volume of tissue being treated. By way of example only, a device configured for use in tumors or other large lesions (e.g., greater than 3 cm in diameter) can have temperature sensors positioned at intervals of about 1 cm to about 5 cm both proximally and distally from an ablation element. By way of further example, smaller devices, such as a catheter-based device configured for use in treating ventricular tachycardia, can have temperature sensors positioned at intervals of about 2 mm to about 3 mm both proximally and distally from an ablation element.

Figure 8:
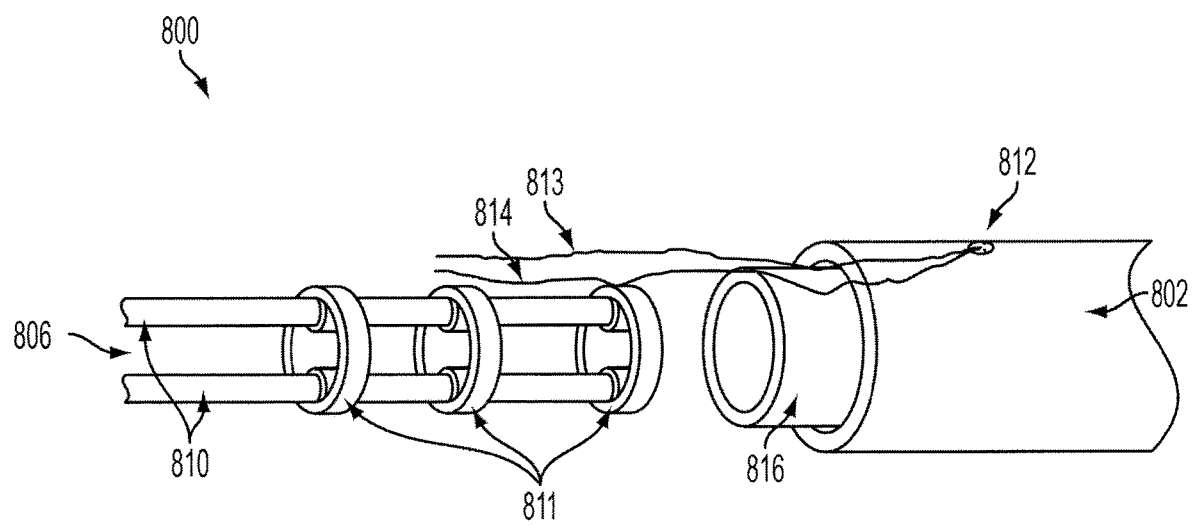
FIG. 8 is an exploded perspective view of one embodiment of an elongate body having a thermocouple embedded in a sidewall thereof.

FIG. 8 illustrates an exploded view showing one embodiment of the construction of a fluid enhanced ablation device 800. An elongate body 802 is shown having an inner lumen 806 that houses components configured to deliver therapeutically heated fluid to the surrounding tissue. For example, the inner lumen 806 can include a dual-wire heating assembly 810 that is configured to heat fluid flowing through the inner lumen 806 by passing electrical energy between the two wires and through the fluid. The dual-wire heating assembly 810 can include one or more spacers 811 configured to hold the two wires of the heating assembly 810 in a substantially fixed geometric relationship with respect to each other and/or the elongate body 802. An exemplary dual-wire heating assembly 810 is described in further detail in U.S. application Ser. No. 13/445,036, issued as U.S. Pat. No. 9,138,287, entitled "Methods and Devices for Heating Fluid in Fluid Enhanced Ablation Therapy," filed concurrently with the present application and incorporated by reference above.

As shown in FIG. 8, the elongate body 802 can include a temperature sensor 812 embedded in a sidewall of the elongate body. The temperature sensor 812 shown is a fine-wire thermocouple known in the art that utilizes different conducting materials to produce a voltage proportional to a temperature difference between the ends of the materials. For example, the thermocouple can include a chromel (Nickel-Chromium alloy) wire 813 and a constantan (Copper-Nickel alloy) wire 814 connected at the location of the thermocouple 812.

The thermocouple or other temperature sensor can be positioned along the elongate body 802 in a variety of manners. For example, the sensor can be placed on an outer surface of the elongate body and any connecting wires can be run through the elongate body and up the inner lumen 806, or the wire can be run along an outer surface of the elongate body 802. In other embodiments, the elongate body 802 can include outer facing grooves, inner facing grooves, or passages formed through a sidewall thereof (depending on the thickness of the sidewall) adapted to accommodate wires connecting to one or more temperature sensors. In still other embodiments, wireless temperature sensors can be positioned along the elongate body 802 to remove the need to run connecting wires to a proximal end of the elongate body.

In the embodiment shown in FIG. 8, the thermocouple temperature sensor 812 is shown embedded in the sidewall of the elongate body 802. By way of example only, the temperature sensor 812 can be embedded by forming a hole in a sidewall of the elongate body 802, placing the thermocouple junction in the hole, and sealing the wires in place with a conductive epoxy. In one exemplary embodiment, a 0.8 mm diameter hole can be formed in a 25 cm long 16-gauge thin-walled stainless steel elongate body, and a thermocouple formed from 0.08 mm diameter Type E (chromel constantan) wires can be placed in the hole and sealed with epoxy. In other embodiments, however, the thermocouple sensor can be affixed to the inside of a thermally conductive elongate body to detect the temperature in the surrounding tissue through the elongate body. In such embodiments, calibration may be necessary to compensate for the indirect measurement.

The embedding procedure described above places the temperature sensor at one given location along the length of the elongate body. In other embodiments, however, one or more temperature sensors can be configured to be adjustable along the length of the elongate body. This can be accomplished, for example, by placing one or more temperature sensors in grooves or tracks running along the length of the elongate body. Alternatively, one or more temperature sensors can be placed on one or more bands disposed around the elongate body that can be slidably moved up and down the length of the elongate body. In still other embodiments, the elongate body can be formed with a plurality of recesses configured to removably receive a temperature sensor module. The recesses can be formed at a variety of spaced apart positions such that a user can select the most appropriate recess for temperature sensor placement prior to ablation therapy. The remaining recesses can be left empty or filled with a plug to maintain the smooth profile of the elongate body. Regardless of the particular implementation, connecting wires from any temperature sensors can be run along an outer surface of the elongate body or can extend into the inner lumen at a particular location along the elongate body. Still further, in some embodiments, wireless temperature sensors can be employed to remove the need for connecting wires.

The inner lumen 806 of the elongate body 802 can also include an insulating tube 816 that houses the dual-wire heating assembly 810 and that contains any fluid flowing through the inner lumen 806. The insulating tube 816 can prevent the temperature of the flowing fluid from affecting the temperature measured by the thermocouple 812. The insulating tube 816 can be formed from any number of thermally insulating materials and, in one embodiment, can be formed from a polymer such as polyimide.

In some embodiments, the insulating tube 816 can be constructed so as to utilize the relatively efficient thermal insulating properties of air. For example, FIG. 9A illustrates one embodiment of an insulating tube 916 having a central lumen 906 and a plurality of secondary lumens 918 formed in a sidewall thereof. Such an insulating tube 916 can be formed, for example, by extrusion methods known in the art. In some embodiments that include the insulating tube 916, the wires associated with one or more of the thermocouples can be run outside the tube 916 or through one of the secondary lumens 918.

In another embodiment illustrated in FIG. 9B, an insulating tube 920 can be formed with one or more features configured to create an air gap between the tube and the sidewalls of the elongate body 802. The insulating tube 920 can include, for example, a plurality of tabs 922 running longitudinally along the tube and extending laterally therefrom. When placed within the inner lumen 806 of the elongate body 802, the tabs 922 can prevent the insulating tube 920 from directly contacting the sidewalls of the elongate body. As a result, an air gap 924 can be created between the thermocouple 812 or other temperature sensor and the insulating tube 920 containing heated fluid for use in fluid enhanced ablation.

The degree of thermal isolation of the flowing saline from the one or more temperature sensors can vary according to the particular design of a given device. In some embodiments, it can be desirable to achieve a particular degree of thermal isolation. This can be quantified, for example, as a difference between a first temperature recorded with no fluid flow through the inner lumen and a second temperature recorded with room temperature saline flowing through the inner lumen. In some embodiments, devices can be configured to limit this difference to 2° C. or less.

The flowing fluid utilized during ablation therapy is not the only thermal interference that can affect the one or more temperature sensors. The elongate body itself can, in some embodiments, affect the temperature measured by the thermocouple 812 or other temperature sensor. For example, in embodiments in which the elongate body 802 is formed from a conducting material, the elongate body itself is likely to conduct heat along a thermal gradient, thereby "flattening" the gradient that might otherwise be observed in the tissue. This can result in the elongate body being relatively cold while the surrounding tissue is hot at some locations, and vice versa at other locations. This can, in turn, result in the measurement of an incorrect temperature or temperature gradient by the one or more temperature sensors positioned along the length of the elongate body.

The influence of the elongate body on temperatures measured by the one or more temperature sensors disposed thereon can be managed using a variety of techniques. For example, the material, cross-sectional size, and sidewall thickness of the elongate body can be selected so as to match the thermal conductivity of the surrounding tissue. This, however, can be a costly, difficult, and time-consuming calibration to make. Alternatively, a variety of methods can be employed to compensate for any thermal interference from the elongate body. These include mathematical analysis to correct for the influence, empirical observation to calibrate the sensors, or controlled experiments to characterize the effect of the elongate body on the temperature measurements.

For example, in some embodiments, it can be desirable to control the error introduced by the elongate body to be below a particular threshold value. For example, in one embodiment, the elongate body and one or more temperature sensors can be calibrated such that the temperature at a position located a distance apart from an ablation element is within 5° C. of the true temperature within the surrounding tissue at the same position.

In still other embodiments, however, the elongate body may not introduce the thermal interference discussed above. For example, in embodiments in which the elongate body is formed from a non-conducting material such as a polymer, the temperature of the elongate body may not affect the readings of any temperature sensors positioned along the elongate body.

The embodiments described above utilize one or more temperature sensors disposed along the elongate body at locations remote from an ablation element to measure the temperature of tissue surrounding the elongate body. As such, the one or more temperature sensors generally provide readings along a longitudinal axis of the elongate body. In other embodiments, however, one or more temperature sensors can be located remotely from both the ablation element and the elongate body itself. Positioning one or more temperature sensors at various locations within the volume of tissue surrounding the elongate body and ablation element can provide data regarding the three-dimensional propagation of thermal energy within the surrounding tissue.

Figure 10:
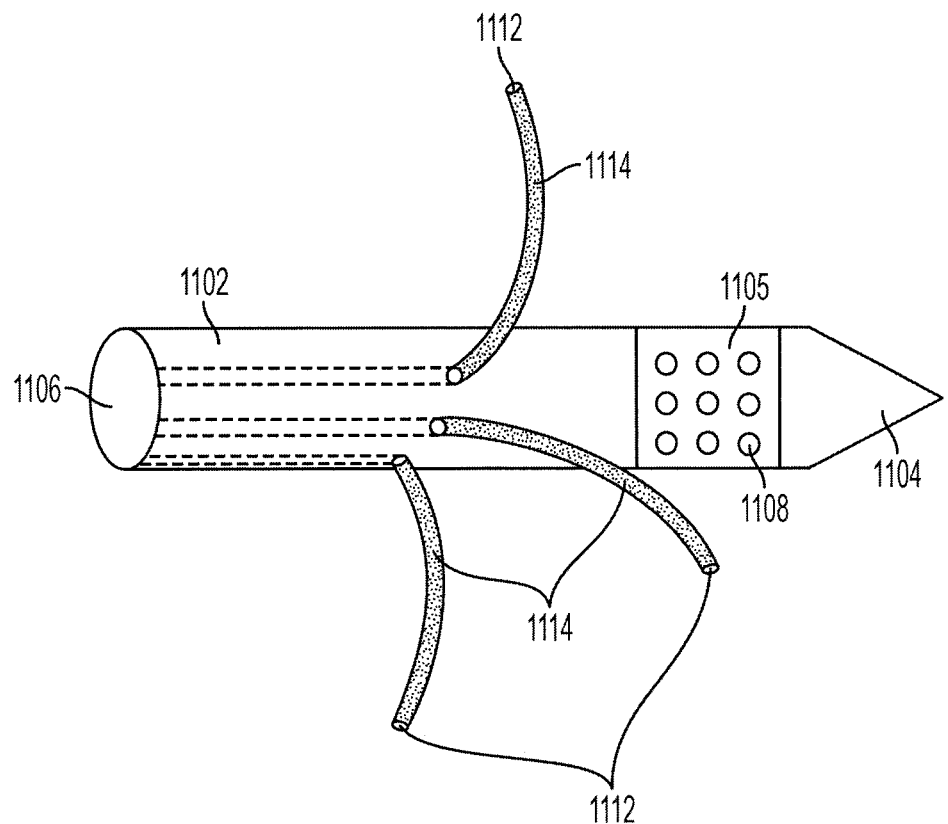
FIG. 10 is a perspective view of one embodiment of an elongate body having thermocouples disposed at the ends of elastic tines extending from the elongate body.

FIG. 10 illustrates one embodiment of a fluid enhanced ablation device including an elongate body 1102 having a distal tip 1104, an ablation element 1105, and one or more outlet ports 1108 formed in the elongate body to deliver fluid from an inner lumen 1106 to tissue surrounding the elongate body. The device also includes a plurality of temperature sensors 1112 each located at a distal end of an elastic tine 1114 that is configured to extend from the elongate body 1102 into surrounding tissue. The elastic tines can be formed from a variety of materials and, in one embodiment, are formed from Nitinol (Nickel-Titanium alloy). The temperature sensors disposed at the distal ends of the elastic tines can be any of the temperature sensors discussed above, for example, fine-wire thermocouples or wireless sensors. If a wired temperature sensor is used, the tines can be formed with an inner lumen that accommodates the wired connection, or the wires can be run along an outer surface of the tine and affixed thereto using, for example, a thin polymer coating.

In use, the tines 1114 can be initially retracted into the elongate body 1102, with the sensors 1112 disposed within the elongate body 1102, such that they do not interfere with insertion of the elongate body into the desired treatment volume of tissue. The tines 1114 can be housed within passages formed in the sidewall of the elongate body (shown as dotted lines in FIG. 10), or can be housed within the inner lumen 1106 of the elongate body. After the elongate body 1102 is positioned within the treatment volume (e.g., positioned such that the ablation element 1105 is located generally in the center of the treatment volume), the tines 114 can be extended from outlet ports formed in the elongate body 1102 and can assume, for example, the configuration shown in FIG. 10. The temperature sensors 1112 located at the distal end of each tine 1114 can detect the temperature of tissue and determine when a therapeutic dose of ablative energy has been delivered to the entire treatment volume. Following therapy, the tines can be retracted into the elongate member 1102 prior to removing or repositioning the elongate member 1102.

Any number of tines 1114 can be utilized, and the tines can be preconfigured to assume a particular shape within the surrounding tissue using the shape memory characteristics of particular materials such as Nitinol. As a result, a series of tines 1114 can be used to form, for example, a spherical detection pattern surrounding the elongate body 1102. A spherical pattern of temperature sensors can allow a control system or operator to more precisely and accurately determine when a desired treatment volume has received a therapeutic dose of ablative energy.

Figure 11:
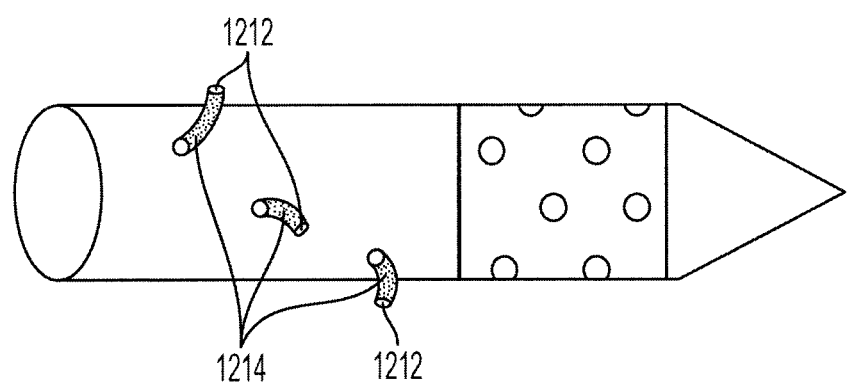
FIG. 11 is a perspective view of an alternative embodiment of an elongate body having thermocouples disposed at the ends of elastic tines extending from the elongate body.

In addition to providing three-dimensional data regarding the temperature of tissue surrounding the elongate body 1102, the physical separation from the elongate body provided by the elastic tines 1114 can also substantially eliminate the thermal influence of the elongate body and/or flowing fluid discussed above. Accordingly, in some embodiments, shorter elastic tines can be employed to provide thermal isolation while maintaining the proximity of the temperature sensors to the elongate body. An exemplary embodiment is illustrated in FIG. 11, which shows the use of temperature sensors 1212 in combination with very short elastic tines 1214. Moreover, the elastic tines shown in FIGS. 10 and 11 can be combined with any of the previously discussed embodiments to create devices having a plurality of temperature sensors positioned both along an axis of the elongate body and in the tissue surrounding the elongate body.

Still further, each tine can vary in length such that a device can have one or more longer tines and one or more shorter tines. Such a configuration can allow a device to obtain temperatures at a variety of distances from an ablation element or therapeutically heated saline source. Any device incorporating retractable tines with temperature sensors disposed thereon can also include an actuator configured to deploy the tines from the elongate body 1102. Exemplary actuator mechanisms can include a sliding lever, a trigger, etc. Each tine can have its own actuator mechanism or a single mechanism can be used to control and deploy a plurality of tines.

Figure 12:
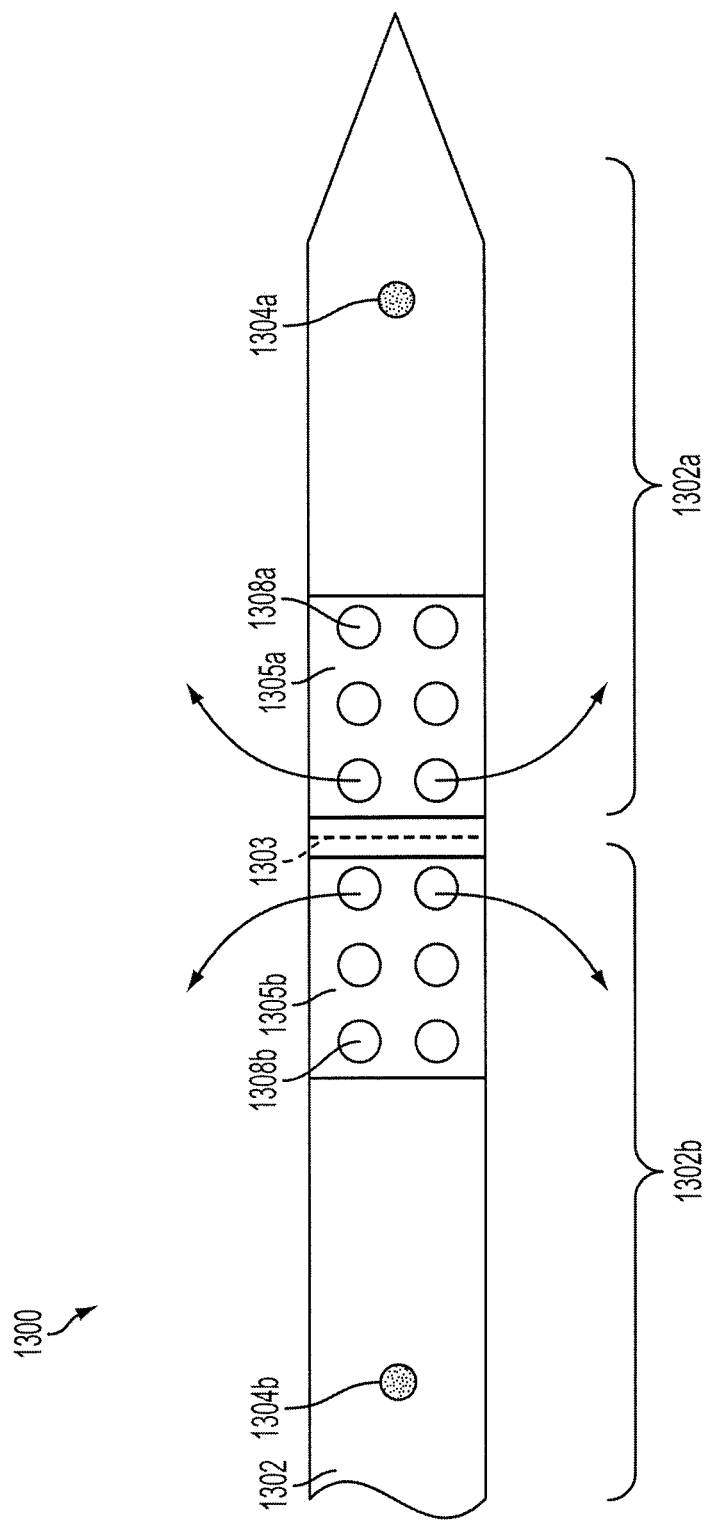
FIG. 12 is a side view of one embodiment of an elongate body having a plurality of ablation elements and temperature sensors.

FIG. 12 illustrates another embodiment of an ablation device 1300 having one or more temperature sensors located a distance apart from an ablation element. The device in FIG. 12 is divided into portions by one or more baffling members. In the illustrated embodiment, the device is divided into a first distal section 1302a and a second proximal section 1302b by a baffling element 1303. The baffling element 1303 can be an inner wall that separates the inner lumen of the first section 1302a of the elongate body from the inner lumen of the second section 1302b of the elongate body.

Each section 1302a, 1302b can include an ablation element, such as an emitter electrode 1305a, 1305b, as well as one or more outlet ports 1308a, 1308b formed along the elongate body 1302 and/or emitter electrode 1305a, 1305b that are in fluid communication with the inner lumen of each section. The sections 1302a, 1302b can further include one or more temperature sensors 1304a, 1304b disposed along the elongate body and configured to detect the temperature of tissue surrounding the elongate body 1302. The temperature sensors can be implemented according to any of the teachings of the present invention and, in some embodiments, the sensors can be fine-wire chromel-constantan thermocouples embedded in a hole formed in the sidewall of the elongate body 1302. The temperature sensors 1304a, 1304b can be positioned at any location along the elongate body 1302 but, in some embodiments, can be positioned symmetrically with respect to, i.e., at an equal distance away from, the ablation elements 1305a, 1305b. This arrangement can allow for a more accurate measurement of the uniformity of expansion of the treatment zone.

Figure 13:
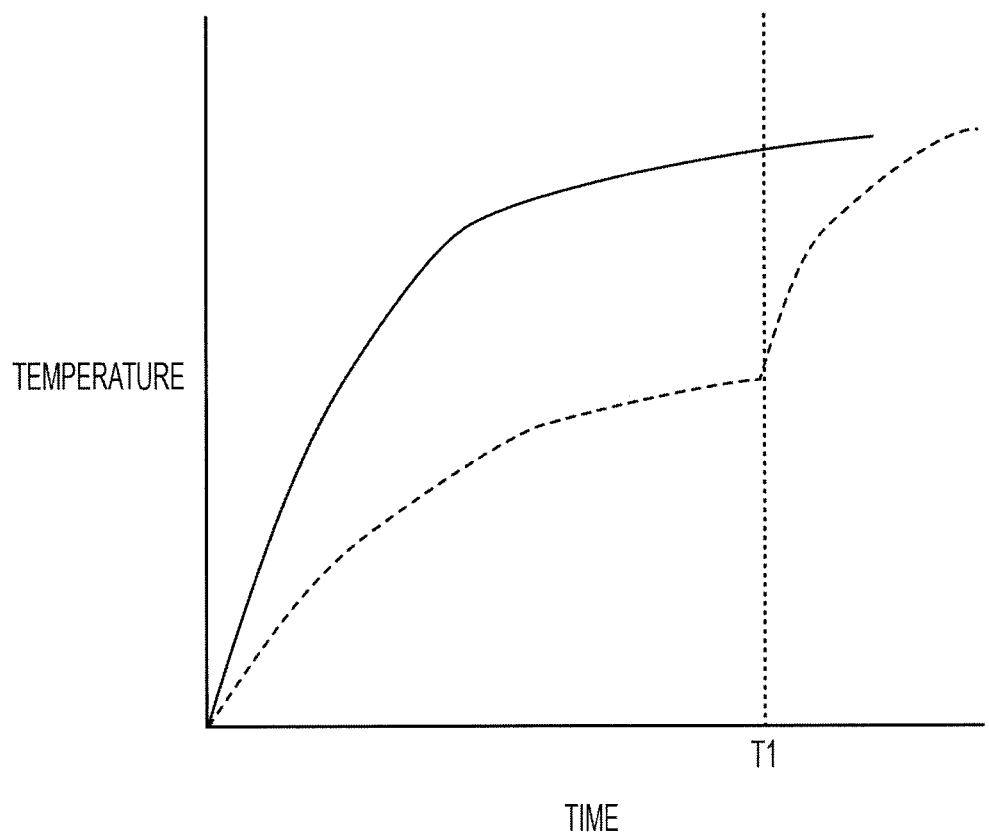
FIG. 13 is a graphical representation of dynamic heating profiles that can be achieved using the elongate body of FIG. 12.

One benefit of the device 1300 illustrated in FIG. 12 is the flexibility provided to dynamically alter the therapy delivered in response to the temperatures detected by the sensors 1304a, 1304b. FIG. 13 shows simulated temperature measurements for the two temperature sensors 1304a, 1304b over time. The solid line represents the temperatures recorded by temperature sensor 1304a during fluid enhanced ablation therapy, and the dashed line represents the temperatures recorded by temperature sensor 1304b. The initial conditions at the beginning of therapy are identical, i.e., the same amount of ablative energy is being delivered from both ablation elements 1305a, 1305b, and the fluid is being delivered from both sections 1302a, 1302b at the same temperature and flow rate. The dashed profile in FIG. 13 clearly shows that uneven heating is occurring in the tissue surrounding the elongate body 1302. Specifically, the tissue surrounding temperature sensor 1304b is not heating to the same therapeutic level as the tissue surrounding temperature sensor 1304a. Accordingly, at time $T_1$ shown in the figure, the operating parameters of the ablation therapy are altered. Any or all of the following steps can be taken: (1) the level of ablative energy can be increased in ablation element 1305b, (2) the flow rate of fluid from section 1302b can be increased, (3) the temperature of the fluid from section 1302b can be increased, (4) the level of ablative energy can be decreased in ablation element 1305a, (5) the flow rate of fluid from section 1302a can be decreased or (6) the temperature of fluid from second 1302a can be decreased or the flow rate can be increased and the temperature decreased (to essentially urge the heated fluid from section 1302b toward the temperature sensor 1304b).

As the example above illustrates, there are a variety of operating parameters for fluid enhanced ablation therapy that can be altered to adjust the therapy delivered to a target volume of tissue. These adjustments can be performed manually by an operator viewing the detected temperatures, or the adjustments can be made automatically by, for example, a control system monitoring the temperature sensors and controlling the therapy operating parameters.

Figure 14:
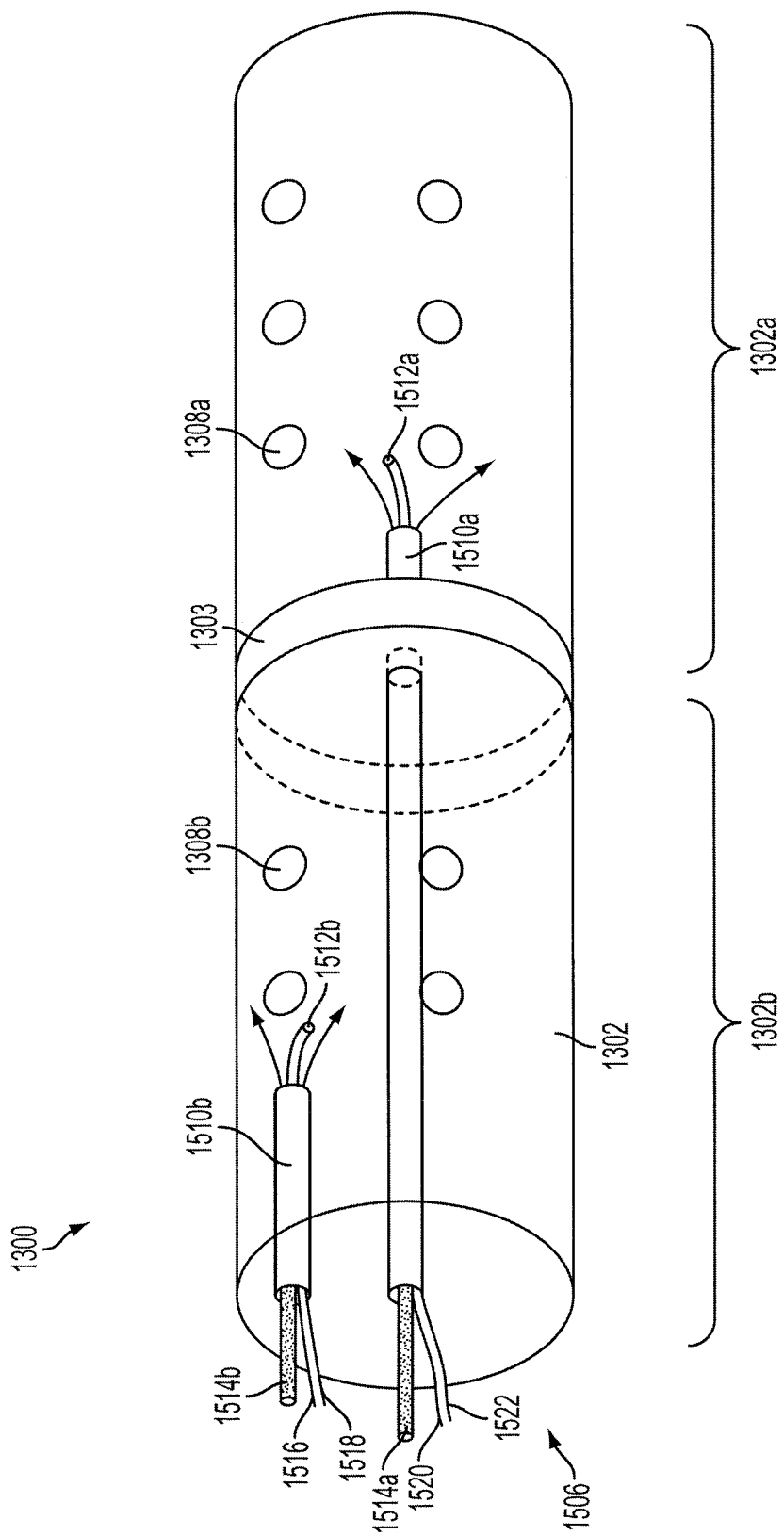
FIG. 14 is a perspective, semi-transparent view of the elongate body of FIG. 12 showing the elongate body divided into portions that can each independently receive fluid at a given temperature.

FIG. 14 illustrates a semi-transparent view of the device of FIG. 12 and shows one embodiment of the internal construction of the elongate body divided into a plurality of sections by one or more baffling members 1303. As shown in the figure, the inner lumen of section 1302a can be separated from section 1302b by the baffling member 1303. The baffling member 1303 can be constructed in a variety of manners. For example, the baffling member can be an integrated portion of the elongate body 1302, or it can be a separate component secured in the inner lumen 1506 of the elongate body 1302 by an adhesive or other retaining component or material. The baffle 1303 can be formed, for example, from a plastic or other suitable material.

The baffling element 1303 can further include one or more lumens formed therein that are each configured to receive a cannula, such as cannula 1510a. The cannula 1510a can be formed from metal, plastic, or plastic having a metal lining, and can include an inner lumen that provides a fluid passageway to the proximal end of the device 1300 through any intervening baffles (e.g., the baffle 1303) and sections (e.g., the second section 1302b). The inner lumen of the cannula 1510a is not in fluid communication with the inner lumen of any other section (e.g., section 1302b). This allows, for example, fluid to be delivered into section 1302a separately from the fluid delivered to section 1302b, e.g., separate fluid sources can be connected to each section, or the sections can each independently receive fluid from a single common source. The inner lumen 1506 can also include additional cannulas configured to deliver fluid to other sections of the device 1300. For example, the inner lumen 1506 can include a cannula 1510b configured to deliver fluid from a proximal end of the device 1300 into the second section 1302b of the device 1300.

One skilled in the art will appreciate that the inner lumen 1506 can include as many cannulas as there are sections in the device. Further, the device 1300 can have any number of sections depending on the desired shape of the treatment zone. For example, the device 1300 can include two sections as illustrated in FIG. 12, or can have three or more sections.

In addition, the cannulas can each be rigidly held in position by a spacer element (e.g., an element similar to the baffle 1303 but also including one or more lumens to allow the passage of fluid around the baffle) or can be allowed to float in the inner lumen 1506. In other embodiments, the cannulas can include features formed on an external surface thereof to prevent contact with other cannulas or the inner walls of the inner lumen 1506. Exemplary features include fins or ribs formed on the outer surface of the cannulas.

Each cannula 1510a, 1510b can be connected at a proximal end to an independent fluid source. Each cannula 1510a, 1510b can also include an independent heating assembly disposed within the inner lumen of the cannula near its distal end. An exemplary heating assembly can include, for example, a single wire 1514a, 1514b running through the inner lumen of the cannula 1510a, 1510b that is configured to pass RF energy through fluid within the inner lumen of the cannula into the inner wall of the cannula 1510a, 1510b. The wire 1514a, 1514b can include one or more spacers disposed thereon to prevent the wire from directly contacting the conductive portion of the cannula 1510a, 1510b. A more detailed description of such a heating assembly can be found in U.S. application Ser. No. 13/445,036, issued as U.S. Pat. No. 9,138,287, entitled "Methods and Devices for Heating Fluid in Fluid Enhanced Ablation Therapy," filed concurrently with the present application and incorporated by reference above.

The heating assembly described above requires that each cannula 1510a, 1510b be at least partially formed from an electrically conductive material (to receive RF energy from the wire 1514a, 1514b). In such an embodiment, the cannulas 1510a, 1510b can be coated in an insulating material so as to prevent any electrical shorts due to contact with each other or the inner walls of the inner lumen 1506 of the device 1300. In addition, a thermally insulating material can also be used to coat the cannulas 1510a, 1510b to prevent the temperature of fluid in any one section from influencing the temperature of fluid in other sections. However, in some embodiments, the fluid flow rate can be high enough that fluid does not spend enough time in any one section to influence, or be influenced by, the temperature of fluid in that section. In these embodiments, thermal insulation of the cannulas 1310a, 1310b is not necessary.

The cannulas 1510a, 1510b can also include a temperature sensor configured to provide feedback regarding the temperature of fluid being delivered to a section of the device 1300. For example, the cannula 1510a can include a dual-wire thermocouple 1512a configured to extend beyond the distal end of the cannula 1510a such that the thermocouple can measure the temperature of fluid within the first section 1302a after it exits the cannula and mixes within the inner lumen 1506 before exiting into the surrounding tissue through the outlet ports 1308a. The two thermocouple wires 1520, 1522 can extend through the inner lumen of the cannula 1510a back to the proximal end of the device 1510a. The wires can be connected to signal processing electronics as known in the art to determine the temperature of the fluid in the first section 1302a. As shown in the figure, the second cannula 1510*b* can also include a temperature sensor 1512*b*, such as a dual-wire thermocouple formed from two wires 1516, 1518. The sensor 1512*b* can similarly be configured to extend beyond the distal end of the cannula 1510*b* into the second section 1302*b* such that the temperature measured by the sensor 1512*b* represents the temperature of mixed fluid that is about to be delivered into surrounding tissue via outlet ports 1308*b*. One skilled in the art will appreciate that a variety of temperature sensors can be employed in the devices of the present invention, including, for example, chromel-constantan fine-wire thermocouples.

Methods of Use

The various embodiments of the devices and systems disclosed herein can be utilized in a variety of surgical procedures to treat a number of medical conditions. For example, medical devices as disclosed herein can be configured for insertion into a target volume of tissue directly during an open surgical procedure. Alternatively, the medical devices can be configured to be passed through one or more layers of tissue during a laparoscopic or other minimally invasive procedure. Furthermore, the devices can be configured for introduction into a patient via an access port or other opening formed through one or more layers of tissue, or via a natural orifice (i.e., endoscopically). Following delivery to a treatment site, a portion of a surgical device, e.g., a distal portion of the elongate body 102, can be inserted into a target treatment volume such that an ablation element is disposed within the treatment volume. In some embodiments, the ablation element can be positioned near the center of the treatment volume. If there are any extendable members, such as elastic tines having temperature sensors on a distal end thereof, they can be deployed into the tissue surrounding the elongate member.

Once the device and any associated temperature sensors are positioned within the treatment volume, ablative energy and fluid heated to a therapeutic temperature can be simultaneously delivered through the devices into the treatment volume. In some embodiments, however, therapeutically heated fluid alone can be used without ablative energy. One or more temperature sensors associated with the device can monitor the temperature of tissue at various locations within the target treatment volume. The detected temperatures can be displayed to an operator or monitored by a control program administering the ablation therapy. In some embodiments, the temperatures measured at locations a distance apart from an ablation element can be compared to temperatures measured at or immediately adjacent to the ablation element.

Any anomalies detected during therapy, such as uneven heating in certain portions of the target volume, can be addressed by the operator or control system. Addressing a detected heating anomaly can involve simply maintaining the therapy until all temperature readings report a uniformly delivered therapeutic dose, or it can require the alteration of other therapy operating parameters such as ablative energy level, fluid flow rate, fluid temperature, etc. These parameters can be adjusted individually or in combination by either an operator or control system, as described above.

After a period of time, or depending on one or more feedback indications (e.g., a particular indication from all temperature sensors disposed within the treatment volume, or a particular comparison between two or more measurements), the delivery of ablative energy and fluid can be stopped. Any extending temperature sensors can be retracted into the ablation device, and the device can then be removed and/or repositioned if additional therapy is required.

Sterilization and Reuse

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

For example, the surgical devices disclosed herein may be disassembled partially or completely. In particular, the elongate body 202 of the medical device 200 shown in FIG. 2 may be removed from the handle 204, or the entire handle and elongate body assembly may be decoupled from the electrical and fluid connections 206, 208. In yet another embodiment, the handle, elongate body, and connections may be removably coupled to a housing that contains, for example, the fluid reservoir, pump, and power supply and controller shown in FIG. 1.

Preferably, the devices described herein will be processed before surgery. First, a new or used instrument can be obtained and, if necessary, cleaned. The instrument can then be sterilized. In one sterilization technique, the instrument is placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility.

In many embodiments, it is preferred that the device is sterilized. This can be done by any number of ways known to those skilled in the art including beta or gamma radiation, ethylene oxide, steam, and a liquid bath (e.g., cold soak). In certain embodiments, the materials selected for use in forming components such as the elongate body may not be able to withstand certain forms of sterilization, such as gamma radiation. In such a case, suitable alternative forms of sterilization can be used, such as ethylene oxide.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An ablation device, comprising:
   an elongate body having an inner lumen configured to deliver fluid to tissue surrounding the elongate body through at least one outlet port formed in the elongate body when the elongate body is introduced into a tissue mass;
   at least one ablation element configured to heat tissue within a treatment zone surrounding the elongate body;

a plurality of temperature sensors coupled to the elongate body such that each sensor contacts a sidewall of the elongate body, the plurality of temperature sensors being positioned axially along the elongate body such that each of the plurality of temperature sensors is a distance apart from the at least one ablation element and is effective to output a measured temperature of tissue spaced a distance apart from tissue adjacent to the at least one ablation element such that the measured temperature indicates whether tissue is being heating to a therapeutic level;

an insulating tube extending through the inner lumen of the elongate body, wherein the insulating tube contains the fluid flowing through the inner lumen and prevents the fluid from contacting the sidewall of the elongate body; and a fluid heating assembly disposed within the insulating tube, the fluid heating assembly including one or two wires configured to heat surrounding fluid, the one or two wires extending through at least one spacer disposed within the insulating tube.

2. The ablation device of claim 1, wherein the insulating tube includes a plurality of lumens formed in a sidewall of the insulating tube that surround a central lumen configured to carry the fluid.

3. The ablation device of claim 1, wherein the insulating tube includes a plurality of tabs running longitudinally along the tube and extending laterally therefrom to prevent a sidewall of the insulating tube from contacting the elongate body.

4. The ablation device of claim 1, wherein the plurality of temperature sensors are positioned proximal to the at least one ablation element.

5. The ablation device of claim 1, wherein the plurality of temperature sensors are positioned distal to the at least one ablation element.

6. The ablation device of claim 1, wherein each of the plurality of temperature sensors is positioned at a different distance from the at least one ablation element than a remainder of the plurality of temperature sensors.

7. The ablation device of claim 1, wherein the at least one ablation element comprises a first ablation element and a second ablation element positioned distal to the first ablation element, and the elongate body further includes:
a baffling element disposed within the inner lumen between the first and second ablation elements, the baffling element dividing the inner lumen into a first section proximal of the baffling element and a second section distal of the baffling element; and
a plurality of cannulas extending from a proximal end of the elongate body through the baffling element to allow delivery of separate fluids to each section of the inner lumen.

8. The ablation device of claim 7, wherein the plurality of temperature sensors includes a first plurality of temperature sensors disposed proximal to the first ablation element and a second plurality of temperature sensors disposed distal to the second ablation element.

9. The ablation device of claim 1, wherein the plurality of temperature sensors comprises a first plurality of temperature sensors positioned distal of the at least one ablation element, and a second plurality of temperature sensors positioned proximal of the at least one ablation element.

10. The ablation device of claim 1, wherein the plurality of temperature sensors are located on an outer surface of the elongate body.

11. The ablation device of claim 1, wherein the plurality of temperature sensors are located in the inner lumen of the elongate body.

12. The ablation device of claim 1, wherein the plurality of temperature sensors are each located in a recess formed in the elongate body.

13. The ablation device of claim 1, wherein the plurality of temperature sensors are each thermally isolated from the elongate body.

14. The ablation device of claim 1, wherein a position of at least one of the plurality of temperature sensors is adjustable along a length of the elongate body.

15. The ablation device of claim 1, wherein at least one of the plurality of temperature sensors comprises a thermocouple.

16. A system for delivering saline enhanced ablation, comprising:
an elongate body having an inner lumen and at least one outlet port;
at least one ablation element configured to heat tissue adjacent to the elongate body;
a fluid source in communication with the inner lumen of the elongate body and configured to deliver fluid through the inner lumen such that the fluid can flow through the at least one outlet port and be delivered to tissue;
a plurality of temperature sensors coupled to the elongate body such that each sensor contacts a sidewall of the elongate body, the plurality of temperature sensors being positioned axially along the elongate body such that each of the plurality of temperature sensors is a distance apart from the at least one ablation element and is effective to measure a temperature of tissue spaced a distance apart from tissue adjacent to the at least one ablation element;
an insulating tube extending through the inner lumen of the elongate body, wherein the insulating tube contains the fluid flowing through the inner lumen and prevents the fluid from contacting the sidewall of the elongate body;
a fluid heating assembly disposed within the insulating tube, the fluid heating assembly including one or two wires configured to heat surrounding fluid, the one or two wires extending through at least one spacer disposed within the insulating tube; and
a control unit configured to obtain a temperature of the at least one ablation element and a plurality of temperatures measured by the plurality of temperature sensors;
wherein the plurality of temperatures measured by the plurality of temperature sensors indicate whether tissue within a treatment zone is being heated to a therapeutic level.

17. The system of claim 16, wherein the insulating tube includes a plurality of lumens formed in a sidewall of the insulating tube that surround a central lumen configured to carry the fluid.

18. The system of claim 16, wherein the insulating tube includes a plurality of tabs running longitudinally along the tube and extending laterally therefrom to prevent a sidewall of the insulating tube from contacting the elongate body.

19. The system of claim 16, wherein the control unit is configured to adjust at least one of a flow rate of the fluid flowing through the elongate body, an ablative energy level of the ablation element, and a temperature of the fluid being delivered in response to the plurality of temperatures measured by the plurality of temperature sensors.

\* \* \* \* \*